(12) United States Patent
Navarro et al.

(10) Patent No.: US 7,763,075 B2
(45) Date of Patent: Jul. 27, 2010

(54) ARTIFICIAL DISC PROSTHESIS

(75) Inventors: Richard R. Navarro, Strongsville, OH (US); Bharadwaj Ananthan, Akron, OH (US); Randall R. Theken, Coventry Township, OH (US)

(73) Assignee: Theken Spine, LLC, Akron, OH (US)

( * ) Notice: Subject to any disclaimer, the term of this patent is extended or adjusted under 35 U.S.C. 154(b) by 172 days.

(21) Appl. No.: 11/361,131

(22) Filed: Feb. 24, 2006

(65) Prior Publication Data
US 2006/0259143 A1    Nov. 16, 2006

Related U.S. Application Data

(63) Continuation of application No. 10/552,094, filed as application No. PCT/US2004/010000 on Apr. 2, 2004.

(60) Provisional application No. 60/460,613, filed on Apr. 4, 2003.

(51) Int. Cl.
*A61F 2/44* (2006.01)
(52) U.S. Cl. ............... 623/17.15; 623/17.11; 623/17.16
(58) Field of Classification Search ............... 606/61; 623/17.11–17.16
See application file for complete search history.

(56) References Cited

U.S. PATENT DOCUMENTS

| | | |
|---|---|---|
| 4,057,857 A | 11/1977 | Fettel |
| 4,241,463 A | 12/1980 | Khovaylo |
| 4,688,000 A | 8/1987 | Donovan |
| 4,714,468 A | 12/1987 | Wang et al. |
| 4,714,469 A | 12/1987 | Kenna |
| 4,759,769 A | 7/1988 | Hedman et al. |
| 4,863,477 A | 9/1989 | Monson |
| 4,874,389 A | 10/1989 | Downey |
| 4,911,718 A | 3/1990 | Lee et al. |

(Continued)

FOREIGN PATENT DOCUMENTS

EP    0747025    12/1996

(Continued)

OTHER PUBLICATIONS

Charles Elwood Carlson, Measurement of Pressure Distribution in the Human Hip Joint, Thesis submitted in partial fulfillment of the requirements for the Degree of Master of Science, May 1967, pp. i-vi and 1-49, Charles Elwood Carlson, U.S.A.

(Continued)

*Primary Examiner*—Eduardo C Robert
*Assistant Examiner*—Julianna N Harvey
(74) *Attorney, Agent, or Firm*—Middleton Reutlinger; Robert H. Eichenberger; Eric L. Killmeier

(57) ABSTRACT

A visco-elastic motion-limiting artificial intervertebral disc prosthesis is provided that mimics the physiologic function of a normal spinal disc. The disc comprises upper and lower endplates having therewithin channels or openings for optionally receiving one or more motion-limiting members fitted on each end with an enlarged portion. One or more compression stops is provided between the upper and lower endplates. Additionally, an elastomeric cushion is disposed between the endplates and surrounds the motion-limiting members. Also, force transducers and microelectronics can be utilized to provide data to the surgeon or the patient regarding the load state of the disc.

26 Claims, 30 Drawing Sheets

U.S. PATENT DOCUMENTS

| | | | |
|---|---|---|---|
| 4,932,969 A | 6/1990 | Frey et al. | |
| 4,946,378 A | 8/1990 | Hirayama et al. | |
| 4,997,432 A | 3/1991 | Keller | |
| 5,002,576 A * | 3/1991 | Fuhrmann et al. | 623/17.15 |
| 5,035,716 A | 7/1991 | Downey | |
| 5,062,850 A | 11/1991 | MacMillan et al. | |
| 5,071,437 A * | 12/1991 | Steffee | 623/17.16 |
| 5,123,926 A | 6/1992 | Pisharodi | |
| 5,171,281 A | 12/1992 | Parsons et al. | |
| 5,197,488 A * | 3/1993 | Kovacevic | 600/595 |
| 5,246,458 A | 9/1993 | Graham | |
| 5,258,031 A | 11/1993 | Salib et al. | |
| 5,300,120 A | 4/1994 | Knapp et al. | |
| 5,314,477 A * | 5/1994 | Marnay | 623/17.15 |
| 5,320,644 A | 6/1994 | Baumgartner | |
| 5,326,363 A | 7/1994 | Aikins | |
| 5,370,697 A | 12/1994 | Baumgartner | |
| 5,401,269 A | 3/1995 | Butner-Janz et al. | |
| 5,425,773 A | 6/1995 | Boyd et al. | |
| 5,456,724 A | 10/1995 | Yen et al. | |
| 5,458,642 A | 10/1995 | Beer et al. | |
| 5,476,465 A | 12/1995 | Preissman | |
| 5,511,561 A | 4/1996 | Wanderman et al. | |
| 5,514,180 A | 5/1996 | Heggeness et al. | |
| 5,534,030 A | 7/1996 | Navarro et al. | |
| 5,536,270 A | 7/1996 | Songer et al. | |
| 5,545,229 A | 8/1996 | Parsons et al. | |
| 5,556,431 A | 9/1996 | Buttner-Janz et al. | |
| 5,562,738 A | 10/1996 | Boyd et al. | |
| 5,674,294 A * | 10/1997 | Bainville et al. | 623/17.16 |
| 5,674,296 A | 10/1997 | Bryan et al. | |
| 5,676,701 A | 10/1997 | Yuan | |
| 5,676,702 A | 10/1997 | Ratron | |
| 5,683,465 A | 11/1997 | Shinn et al. | |
| 5,702,450 A | 12/1997 | Bisserie | |
| 5,749,909 A | 5/1998 | Schroeppel et al. | |
| 5,782,832 A | 7/1998 | Larsen et al. | |
| 5,824,094 A | 10/1998 | Serhan et al. | |
| 5,827,328 A | 10/1998 | Buttermann | |
| 5,865,846 A | 2/1999 | Bryan et al. | |
| 5,888,226 A | 3/1999 | Rogozinski | |
| 5,893,889 A * | 4/1999 | Harrington | 623/17.16 |
| 5,906,643 A | 5/1999 | Walker | |
| 5,928,284 A | 7/1999 | Mehdizadeh | |
| 5,935,171 A | 8/1999 | Schneider et al. | |
| 5,977,431 A | 11/1999 | Knapp et al. | |
| 6,001,130 A | 12/1999 | Bryan et al. | |
| 6,019,792 A | 2/2000 | Cauthen | |
| 6,034,296 A | 3/2000 | Elvin et al. | |
| 6,039,763 A | 3/2000 | Shelokov | |
| 6,059,784 A | 5/2000 | Perusek | |
| 6,063,121 A | 5/2000 | Xavier et al. | |
| 6,086,613 A | 7/2000 | Camino et al. | |
| 6,093,205 A | 7/2000 | McLeod et al. | |
| 6,115,636 A | 9/2000 | Ryan | |
| 6,136,031 A | 10/2000 | Middleton | |
| 6,139,579 A | 10/2000 | Steffee et al. | |
| 6,156,067 A | 12/2000 | Bryan et al. | |
| 6,162,252 A | 12/2000 | Kuras et al. | |
| 6,170,488 B1 | 1/2001 | Spillman et al. | |
| 6,179,874 B1 | 1/2001 | Cauthen | |
| 6,216,537 B1 | 4/2001 | Henschel et al. | |
| 6,231,609 B1 | 5/2001 | Mehdizadeh | |
| 6,296,664 B1 | 10/2001 | Middleton | |
| 6,315,797 B1 | 11/2001 | Middleton | |
| 6,348,071 B1 | 2/2002 | Steffee et al. | |
| 6,366,206 B1 | 4/2002 | Ishikawa et al. | |
| 6,368,350 B1 | 4/2002 | Erickson et al. | |
| 6,395,034 B1 | 5/2002 | Suddaby | |
| 6,402,785 B1 | 6/2002 | Zdeblick et al. | |
| 6,419,704 B1 | 7/2002 | Ferree | |
| 6,425,920 B1 * | 7/2002 | Hamada | 623/17.16 |
| 6,440,168 B1 | 8/2002 | Cauthen | |
| 6,447,448 B1 * | 9/2002 | Ishikawa et al. | 600/300 |
| 6,471,725 B1 | 10/2002 | Ralph et al. | |
| 6,478,822 B1 | 11/2002 | Leroux et al. | |
| 6,482,234 B1 | 11/2002 | Weber et al. | |
| 6,520,996 B1 | 2/2003 | Manasas et al. | |
| 6,527,806 B2 | 3/2003 | Ralph et al. | |
| 6,579,320 B1 | 6/2003 | Gauchet et al. | |
| 6,579,321 B1 | 6/2003 | Gordon et al. | |
| 6,607,558 B2 | 8/2003 | Kuras | |
| 6,610,092 B2 | 8/2003 | Ralph et al. | |
| 6,610,094 B2 | 8/2003 | Husson | |
| 6,626,943 B2 | 9/2003 | Eberlein et al. | |
| 6,645,248 B2 | 11/2003 | Casutt | |
| 6,656,178 B1 | 12/2003 | Veldhuizen et al. | |
| 6,656,224 B2 | 12/2003 | Middleton | |
| 6,669,732 B2 | 12/2003 | Serhan et al. | |
| 6,679,915 B1 | 1/2004 | Cauthen | |
| 6,682,562 B2 | 1/2004 | Viart et al. | |
| 6,692,528 B2 | 2/2004 | Ward et al. | |
| 6,706,068 B2 | 3/2004 | Ferree | |
| 6,723,127 B2 | 4/2004 | Ralph et al. | |
| 6,726,720 B2 | 4/2004 | Ross et al. | |
| 6,733,531 B1 | 5/2004 | Trieu | |
| 6,733,532 B1 | 5/2004 | Gauchet et al. | |
| 6,764,514 B1 | 7/2004 | Li et al. | |
| 6,770,095 B2 | 8/2004 | Grinberg et al. | |
| 6,793,678 B2 | 9/2004 | Hawkins | |
| 7,060,100 B2 | 6/2006 | Ferree et al. | |
| 7,066,958 B2 | 6/2006 | Ferree | |
| 7,201,776 B2 | 4/2007 | Ferree et al. | |
| 7,267,688 B2 | 9/2007 | Ferree | |
| 7,291,171 B2 | 11/2007 | Ferree | |
| 2002/0049394 A1 | 4/2002 | Roy et al. | |
| 2003/0009224 A1 | 1/2003 | Kuras | |
| 2003/0069644 A1 * | 4/2003 | Kovacevic et al. | 623/20.32 |
| 2003/0100951 A1 | 5/2003 | Serhan et al. | |
| 2003/0135277 A1 | 7/2003 | Bryan et al. | |
| 2003/0153976 A1 | 8/2003 | Cauthen, III et al. | |
| 2003/0176921 A1 | 9/2003 | Lawson | |
| 2003/0176923 A1 | 9/2003 | Keller et al. | |
| 2003/0187506 A1 | 10/2003 | Ross et al. | |
| 2003/0191533 A1 | 10/2003 | Dixon et al. | |
| 2003/0191534 A1 | 10/2003 | Viart et al. | |
| 2003/0191536 A1 | 10/2003 | Ferree | |
| 2003/0195630 A1 | 10/2003 | Ferree | |
| 2003/0195631 A1 | 10/2003 | Ferree | |
| 2003/0199981 A1 | 10/2003 | Ferree | |
| 2003/0199982 A1 | 10/2003 | Bryan | |
| 2003/0204231 A1 | 10/2003 | Hine et al. | |
| 2003/0204260 A1 | 10/2003 | Ferree | |
| 2003/0204271 A1 | 10/2003 | Ferree | |
| 2003/0216810 A1 | 11/2003 | Ralph et al. | |
| 2003/0220589 A1 * | 11/2003 | Leivseth et al. | 600/591 |
| 2003/0220691 A1 | 11/2003 | Songer et al. | |
| 2003/0220695 A1 | 11/2003 | Sevrain | |
| 2003/0233097 A1 | 12/2003 | Ferree | |
| 2003/0233146 A1 | 12/2003 | Grinberg et al. | |
| 2003/0233148 A1 | 12/2003 | Ferree | |
| 2003/0236571 A1 | 12/2003 | Ralph et al. | |
| 2004/0002761 A1 | 1/2004 | Rogers et al. | |
| 2004/0002762 A1 | 1/2004 | Hawkins | |
| 2004/0010316 A1 | 1/2004 | William et al. | |
| 2004/0010318 A1 | 1/2004 | Ferree | |
| 2004/0024458 A1 | 2/2004 | Senegas et al. | |
| 2004/0024460 A1 | 2/2004 | Ferree | |
| 2004/0024461 A1 | 2/2004 | Ferree | |
| 2004/0024462 A1 | 2/2004 | Ferree | |
| 2004/0024463 A1 | 2/2004 | Thomas, Jr. et al. | |
| 2004/0030389 A1 | 2/2004 | Ferree | |
| 2004/0030390 A1 | 2/2004 | Ferree | |
| 2004/0030391 A1 | 2/2004 | Ferree | |

| | | | |
|---|---|---|---|
| 2004/0034421 A1 | 2/2004 | Errico et al. | |
| 2004/0034422 A1 | 2/2004 | Errico et al. | |
| 2004/0034423 A1 | 2/2004 | Lyons et al. | |
| 2004/0034424 A1 | 2/2004 | Errico et al. | |
| 2004/0034425 A1 | 2/2004 | Errico et al. | |
| 2004/0034426 A1 | 2/2004 | Errico et al. | |
| 2004/0039448 A1 | 2/2004 | Pisharodi | |
| 2004/0049270 A1 | 3/2004 | Gewirtz | |
| 2004/0049280 A1 | 3/2004 | Cauthen | |
| 2004/0054411 A1 | 3/2004 | Kelly et al. | |
| 2004/0068320 A1 | 4/2004 | Robie et al. | |
| 2004/0068321 A1 | 4/2004 | Ferree | |
| 2004/0073307 A1 | 4/2004 | Keller | |
| 2004/0073310 A1 | 4/2004 | Moumene et al. | |
| 2004/0073311 A1 | 4/2004 | Ferree | |
| 2004/0073312 A1 | 4/2004 | Eisermann et al. | |
| 2004/0078080 A1 | 4/2004 | Thramann et al. | |
| 2004/0093087 A1 | 5/2004 | Ferree et al. | |
| 2004/0093088 A1 | 5/2004 | Ralph et al. | |
| 2004/0098130 A1 | 5/2004 | Ralph et al. | |
| 2004/0098131 A1 | 5/2004 | Bryan et al. | |
| 2004/0102846 A1 | 5/2004 | Keller et al. | |
| 2004/0102849 A1 | 5/2004 | Ralph et al. | |
| 2004/0106995 A1 | 6/2004 | Le Couedic | |
| 2004/0106998 A1 | 6/2004 | Ferree | |
| 2004/0111155 A1 | 6/2004 | Ferree | |
| 2004/0111156 A1 | 6/2004 | Ralph et al. | |
| 2004/0111157 A1 | 6/2004 | Ralph et al. | |
| 2004/0111158 A1 | 6/2004 | Ralph et al. | |
| 2004/0111160 A1 | 6/2004 | Evans et al. | |
| 2004/0117020 A1 | 6/2004 | Frey et al. | |
| 2004/0117021 A1 | 6/2004 | Biedermann et al. | |
| 2004/0117022 A1 | 6/2004 | Marnay et al. | |
| 2004/0122517 A1* | 6/2004 | Kuras | 623/17.11 |
| 2005/0023455 A1 | 2/2005 | Bailey et al. | |
| 2005/0125063 A1 | 6/2005 | Matge et al. | |
| 2005/0143733 A1 | 6/2005 | Petit | |
| 2005/0273170 A1 | 12/2005 | Navarro et al. | |
| 2006/0015183 A1 | 1/2006 | Gilbert et al. | |
| 2006/0036321 A1 | 2/2006 | Henninger et al. | |
| 2006/0106462 A1 | 5/2006 | Tsou | |
| 2006/0142860 A1 | 6/2006 | Navarro et al. | |

FOREIGN PATENT DOCUMENTS

| | | |
|---|---|---|
| EP | 0773008 | 5/1997 |
| EP | 0820740 | 1/1998 |
| EP | 1023011 | 8/2000 |
| EP | 1104665 | 6/2001 |
| EP | 1287795 | 3/2003 |
| EP | 1290993 | 3/2003 |
| EP | 1293180 | 3/2003 |
| EP | 1342456 | 9/2003 |
| EP | 1354572 | 10/2003 |
| EP | 1374807 | 1/2004 |
| EP | 1374809 | 1/2004 |
| EP | 1124509 | 3/2004 |
| EP | 1206227 | 4/2004 |
| EP | 1405615 | 4/2004 |
| WO | WO-9530389 | 11/1995 |
| WO | WO-9623457 | 8/1996 |
| WO | WO-0053127 | 9/2000 |
| WO | WO-0101893 | 1/2001 |
| WO | WO-02076351 | 10/2002 |
| WO | WO-02087480 | 11/2002 |
| WO | WO-03068111 | 8/2003 |
| WO | WO-03068112 | 8/2003 |
| WO | WO-03075803 | 9/2003 |
| WO | WO-03077806 | 9/2003 |
| WO | WO-03090648 | 11/2003 |
| WO | WO-03090649 | 11/2003 |
| WO | WO-03090650 | 11/2003 |
| WO | WO-03092559 | 11/2003 |
| WO | WO-03094805 | 11/2003 |
| WO | WO-03094806 | 11/2003 |
| WO | WO-03099172 | 12/2003 |

OTHER PUBLICATIONS

Charles E. Carlson, An Instrumented Prosthesis for Measuring the Cartilage Surface Pressure Distribution in the Human Hip, Thesis submitted in partial fulfillment of the requirements for the Degree of Doctor of Science, May 5, 1972, pp. 1-185, Charles E. Carlson, U.S.A.

Charles E. Carlson; Robert W. Mann; William H. Harris, A Look at the Prosthesis-Cartilage Interface: Design of a Hip Prosthesis Containing Pressure Transducers, J. Biomed. Mater. Res. Symposium, 1974, pp. 261-269, No. 5 (Part 2), John Wiley & Sons, Inc., U.S.A.

Charles E. Carlson; Robert W. Mann; William H. Harris, A Radio Telemetry Device for Monitoring Cartilage Surface Pressures in the Human Hip, IEEE Transactions on Biomedical Engineering Journal Jul. 1974, vol. BME-21, No. 4, U.S.A.

W.A. Hodge; R.S. Fijan; K.L. Carlson; R.G. Burgess; W.H. Harris; R.W. Mann, Contact pressures in the human hip joint measured in vivo, Proc. Natl. Acad. Sci, USA Journal Biophysics, May 1986, pp. 2879-2883, vol. 83, National Academy of Sciences, U.S.A.

Eric H. Ledet, MS; Barton L. Sachs, MD; John B. Brunski, PHD; Charles E. Gatto, MD; Peter S. Donzelli, PHD, Real-Time In Vivo Loading in the Lumbar Spine, Spine Journal; 2000; pp. 2595-2600, vol. 25, No. 20, Lippincott Williams & Wilkins, Inc., U.S.A.

Alf Nachemson, Lumbar Intradiscal Pressure, Acta Orthopaedica Scandinavica Journal, 1960, pp. 9-104, Supplementum 43, Ejnar Munksgaard, Uppsala, Copenhagen, Sweden.

Lumbar Intradiscal Pressure, The Journal of Bone and Joint Surgery, 1961, p. 414, 43-B(2).

MicroStrain Wireless Sensors Measure 3-D Force and Torque Data in Live Human Knee Replacement, MicroStrain Inc. Press Release, Nov. 3, 2006, Williston, Vermont, USA.

Christopher P. Townsend; Steven W. Arms; Michael J. Hamel, Remotely Powered, Multichannel Microprocessor Based Telemetry Systems for a Smart Implantable Total Knee Implant, MicroStrain Inc. Brochure, SPIE's 6th Annual International Conference on Smart Structures and Materials, Newport Beach, California, Mar. 1-5, 1999, pp. 1-7, Burlington, Vermont, USA.

Beverly A. Morris, MBA, RN; Darryl D. D'Lima, MD; John Slamin; NEB Kovacevic; Steven W. Arms; Christopher P. Townsend; Clifford W. Colwell Jr, MD, e-Knee: Evolution of the Electronic Knee Prosthesis, The Journal of Bone and Joint Surgery, Selected Scientific Exhibits, 2001, pp. 62-66, vol. 83-A, Supplement 2, Part 1, The Morris Agency, San Diego, California, USA.

John A. Engelhardt, Next-Generation Discs, Less Balls, Fewer Sockets, Orthoknow Editorial, Jul. 2004, pp. 4-6, Knowledge Enterprises, Inc., USA.

Robin R. Young, CFA, When a Conference Becomes an Event, Orthopaedics This Week Scientific Paper, May 9, 2005, pp. 1-17, Industry Edition, vol. 1, Issue 11, Robin Young Publications, Wayne, Pennsylvania, USA.

Technology Insights, One Company's Quest to Design a 'Smart' Implant Heralds a New Wave, Horizon Scan Report, Feb. 2007, pp. 1, 7-8, vol. 1, Issue 2, Advisory Board Company, USA.

* cited by examiner

ARTIFICIAL DISC PROSTHESIS

CROSS-REFERENCE TO RELATED APPLICATIONS

This patent application is a continuation of and claims priority to and benefit from, currently pending, U.S. patent application Ser. No. 10/552,094, filed on Oct. 4, 2005, which is a '371 filing from PCT/US2004/010000, filed on Apr. 2, 2004, which is a continuation of U.S. Provisional Patent Application Ser. No. 60/460,613, filed on Apr. 4, 2003.

BACKGROUND OF THE INVENTION

1. Field of the Invention

This invention relates to an artificial visco-elastic, constrained motion disc for replacing intervertebral discs in the lower back, particularly in the lumbar and lumbar-sacral regions.

2. Background

The human spine is composed of many vertebral bones stacked one upon the other, with an intervertebral disc between each pair of adjacent vertebral bones. The discs act as cartilaginous cushions and shock absorbers. The spinal cord runs in a bony canal formed by successive openings in these bones. The spinal nerves exit the spinal cord between pairs of vertebrae and supply nerves and nerve signals to and from other body structures.

The intervertebral disc is a complex joint both anatomically and functionally. It is composed of three component structures: the nucleus pulposus; the annulus fibrosus, and the vertebral endplates. The biomedical composition and anatomical arrangements within these component structures are related to the biomechanical function of the disc.

The nucleus pulposus, occupying about 25% to 40% of the total disc cross-sectional area, usually contains approximately 70% to 90% water by weight. Because of this high water content, the nucleus may be mechanically described as an incompressible hydrostatic material.

The annulus fibrosus is a concentrically laminated structure which contains highly aligned collagen fibers and fibrocartilage embedded in an amorphous ground substance. The annular layers are oriented at approximately +/−60° to the longitudinal axis of the spine. The annulus fibrosus usually contains approximately 8 to 12 layers, and is mechanically the main stabilizing structure which resists torsional and bending forces applied to the disc.

The two vertebral endplates separate the disc from the adjacent vertebral bodies, and are composed of hyaline cartilage.

Spinal discs may be damaged or displaced due to trauma or disease. In either case, the nucleus pulposus may herniate and protrude into the vertebral canal or intervertebral foramen. This condition is known as a herniated or "slipped" disc. The disc may in turn press upon the spinal nerve that exits the vertebral canal through the partially obstructed foramen, causing pain or paralysis in the area of its distribution. The most frequent site of occurrence of a herniated disc is in the lower lumbar region. To alleviate this condition, two procedures are common.

First, it may be necessary to remove the involved disc surgically and fuse the two adjacent vertebrae together. Spinal fusion is a good method of eliminating symptoms, but at the expense of total loss of motion of the fused vertebral joint, as well as increased stress in the adjacent segments. In many long-term patients of fused-spinal segments, a detrimental phenomenon has been observed whereby discs adjacent to the fused-spinal segment will have increased motion and stress due to the increased stiffness of the fused segment. This is sometimes referred to as "cascading spine syndrome," where previously normal motion segments above or below a fused segment exhibit spondylolisthesis, or degenerative disc disease due to increased loading.

A second method for alleviating disc problems is insertion of an intervertebral disc replacement. The object of an intervertebral disc replacement is to provide a prosthetic disc that combines both stability to support the high loads of the patient's vertebrae and flexibility to provide the patient with sufficient mobility and proper spinal column load distribution. In attempting to satisfy these competing design requirements, basically four types of artificial intervertebral discs have been developed: elastomer discs, ball and socket discs, mechanical spring discs, and hybrid discs.

Elastomer discs typically include an elastomer cushion which is sandwiched between upper and lower rigid endplates. Elastomer discs can provide cushion or damping functions similar in mechanical behavior to the removed intervertebral disc tissue. However, known elastomer discs experience long-term in-vivo problems stemming from micro-cracking, fixation problems with respect to the endplates, insufficient compression and torsional resistance, and excessive motion which can lead to bulging of the replacement disc and resultant pain for the patient. One hypothesis for the failures of previous elastomer based disc designs is the unlimited potential for strain. High load in vivo events cause subsequent changes in structural characteristics of the elastomer, a characteristic called the Mullins effect. After initial stress softening effects are accounted for, a stable stress strain curve is reached. However, if a new load cycle is encountered exceeding the previous peak strain, the structural properties will again change. This is the rationale for the failure of previous elastomer disc designs and the inspiration for new motion-limited designs.

Ball and socket discs typically incorporate two plate members having cooperating inner ball and socket portions allowing an articulating motion of the members during movement of the spine. These types of discs generally restore spinal motion, but inadequately replicate the natural stiffness of the intervertebral disc. Furthermore, dislocation and wear problems exist with these devices as well as unsatisfactory motion limiting components. Some types also comprise polymers in conjunction with metallic components.

For example, a Link Charite disc includes polyethylene/cobalt chrome molybdenum (CCM) construction. This design restores motion, but in a very unphysiologic manner. The design is essentially a ball and socket joint which does not provide the nonlinear elastic response of the normal disc including hysteresis and therefore shock absorption. As in hip replacements this design is subject to wear and polyethylene debris complications. This disc, which has been extensively implanted in Europe and the United States, relies on a relatively incompressible ultra high molecular weight polyethylene center mating with concave surfaces in cobalt chrome upper and lower endplates. The mating surfaces provide a low friction pseudo ball-socket joint with motion constraints in compression and anterior-posterior as well as lateral translation. The device is totally unconstrained in rotation about its axis, and in tension. Though this device has a semi successful in vivo history, it lacks fundamental stress strain characteristics of the normal disc. Instead, it provides low friction, high movement, non-energy absorbing kinematic function restoration to the spine motion segment. The disc is designed to move freely until limits of travel are reached. The stopping action provided is very abrupt and thus loads the vertebral endplate in a shock-like manner at end-of-travel. This disc imitates a free moving ball and socket joint, not a natural disc that behaves very elastically until annulus fibers play the role of a "limiter". A natural disc is load sharing between the elastic elements and fibrous tissue limiters.

Mechanical spring discs, which generally have only two or three degrees of freedom, typically incorporate one or more coiled springs disposed between metal endplates. These discs generally allow movement of the vertebrae during flexion and extension. However, these types have significant wear problems, as well as problems dealing with in-vivo torsional loads, and overall these discs cannot replicate the six-degree of freedom movement of a natural intervertebral disc.

Hybrid types of discs generally incorporate two or more principals of any of the aforementioned disc types. For example, one common hybrid disc arrangement includes a ball and socket set surrounded by a non-adhered elastomer ring. This hybrid disc is more complex than would be preferred for common usage, and more importantly, the intermittent contact between the ball socket and the elastomer ring that occasionally occurs in-vivo causes critical wear problems.

It is to be recognized that an artificial disc constructed with a polymer between two metal endplates undergoes compression as a result of both gravity and patient activities requiring exertion of energy. Therefore, ideally a disc would include a means of protecting the polymer and the possible bond joint between polymer and metal. Mechanical stops and motion-limiters can be added to maintain the integrity of the prosthesis. Such structures can take the form of rods, tension cables, or other connectors, as well as metal-to-metal contact in compression, to name but a few examples. Moreover, it would be beneficial for a disc also to include a means to convey to surgeons and to patients the actual state of the loads experienced by the device.

As a result, the need exists for an artificial intervertebral disc that more closely imitates a natural disc. This means that the artificial disc should maintain the vertebrae spaced from each other and prevent pinching of nerves or spinal cord. The artificial disc should provide good load distribution. Furthermore, the artificial disc should be sufficiently resilient to accommodate other motions of the spine, including flexion, extension, lateral bending, and rotation, as well as combinations of these motions. In humans, the bony facet joints actually limit the rotational movement. A disc typically need only rotate approximately three degrees. Moreover, the disc should provide restorative force to bias toward the resting position. The artificial disc should be both biocompatible and biostable such that the disc itself or any of its degradation byproducts, if any, do not cause adverse tissue reactions. Ideally, through the use of strain gauges or other means of force transduction, the disc can also provide stored or real-time data to the surgeon and the patient regarding the state of the loads and displacements experienced by the disc.

BRIEF SUMMARY OF THE INVENTION

The present invention is directed to a prosthetic intervertebral disc replacement that restores and preserves the physiologic function of a normal spinal motion segment. The intervertebral disc replacement addresses the detrimental phenomenon of cascading spine syndrome observed in long-term patients with fused-spinal segments. The present intervertebral disc replacement is designed to avoid the need for spinal fusion or at least prolong the need for it. The invention incorporates elements to bear high load in the design, while preserving the ability of the elastomer to provide substantial motion at low to moderate loads. The invention demonstrates the potential to survive high cycle fatigue in bending, compression, and shear along all three mutually orthogonal axes. The motion-limiting features survive high load, low cycle fatigue and preserve the integrity of the elastic range performance of the device.

According to the present invention, once the disc reaches its mechanically constrained limits in compression, bending, and shear, then the elastomer and the bond interface experiences no additional significant loads as the limiter feature will prevent further significant strain. In vivo loading varies by the individual, activity level, and unique high load events. In the present invention, limiting strains prevents the elastomer from continually changing its structural characteristics with each high load event. A stable stress strain characteristic can be reached and predictable disc performance can be achieved.

The present invention is a visco-elastic constrained-motion disc prosthesis generally comprising specially designed rigid upper and lower endplates having therewithin channels or openings for receiving one or more motion-limiting members fitted on each end with an enlarged portion. In some embodiments, the lower surface of the upper endplate contains a first projection therefrom that extends toward the lower endplate. Likewise, the upper surface of the lower endplate can contain a second projection extending toward said upper endplate and substantially aligned with said first projection. The first and second projections terminate to create a gap therebetween, forming a compression stop. Interposed between the upper and lower endplates is an elastomer cushion. Preferably, the elastomer cushion is not in direct contact with either the motion-limiting members or the first or second projections to avoid wear and debris problems.

The gap allows a predetermined amount of axial movement, but no more, between the upper endplate and the lower endplate. As a result, the gap prevents excess compression from occurring, and is usually designed to allow approximately 1 to 2 millimeters of relative movement between the upper and lower endplates. This limits the compressive stresses seen by the elastomer. During most activities of the patient, the elastomer will exclusively carry the load. The compression stop will be engaged typically only during activities of high exertion.

The motion-limiting members with enlarged portions are inserted into internal cavities in the elastomer and link the upper endplate to the lower endplate. The motion-limiting members are dimensioned so as to have a length that is slightly greater than the distance between the lower surface of the upper endplate and the upper surface of the lower endplate (and also preferably slightly less than the overall length of the internal cavities in which they reside). This allows space for the motion-limiting members to move during compression.

In bending, which is the most important movement of an L4-L5 or L5-S1 disc, the motion-limiting members are strategically oriented to resist the tension in the posterior region of the disc. If motion-limiting members are present at the anterior portion of the disc, they float freely in the internal cavities during bending.

The external surfaces of the upper and lower endplates can also be fitted with wedges, spikes, keels, or other appurtenances to aid in attachment to a vertebral body. These appurtenances can also serve as covers to enclose the enlarged portions of the motion-limiting members.

Additionally, some embodiments of the invention utilize strain gauges, pressure transducers, piezoelectric force transducers, or other means of force transduction to provide stored or real-time data to the surgeon or patient of the load state of the disc.

Several commercially available low durometer (i.e., approximately 70-85 A) polyurethanes with a history of animal and human implantation are candidates to be used in a titanium or CoCrMo/elastomer construction. Hybrid discs according to the invention can overcome one of the failure modes of previous artificial disc designs, namely that of delamination and fatigue failure of the bonded interface between the elastomer and metal. This can be accomplished through improved bonding and motion-limiting features, in those embodiments where the visco-elastic cushion is bonded to the endplates. Other embodiments that utilize no bonding between the visco-elastic cushion and the endplates also achieve improved results with motion-limiting features.

These and other benefits are obtained in the many embodiments of the invention. A particularly useful embodiment comprises an artificial intervertebral disc prosthesis having an anterior portion and a posterior portion, further comprising: a first endplate having an upper surface and a lower surface, wherein the first endplate further comprises at least one opening for receiving at least one motion-limiting member; a first projection extending from the lower surface of the first endplate terminating in a first distal end; a second endplate having an upper surface and a lower surface, wherein the second endplate further comprises at least one opening for receiving at least one motion-limiting member; a second projection extending from the upper surface of the second endplate and substantially aligned with the first projection, wherein the second projection terminates at a second distal end to form a gap having a predetermined distance between the first and second distal ends; at least one motion-limiting member received respectively in the at least one opening of the first and second endplates, linking the two endplates and allowing only a predetermined amount of movement thereof; and a visco-elastic cushion between the first endplate and the second endplate, further comprising therein at least one cavity in substantial alignment with the at least one opening in the first endplate and the second endplate through which the motion-limiting member may pass and at least one cavity surrounding the first and second projections.

BRIEF DESCRIPTION OF THE DRAWINGS

The teachings of the present invention can be readily understood by considering the following detailed description in conjunction with the accompanying drawings, in which:

FIG. 3(*a*) is the artificial disc of FIG. 3 showing a second type of appurtenance fitted to the upper and lower endplates;

FIG. 3(*b*) is the artificial disc of FIG. 3 showing a third type of appurtenance fitted to the upper and lower endplates;

FIG. 3(*c*) is the artificial disc of FIG. 3 showing a fourth type of appurtenance fitted to the upper and lower endplates;

DETAILED DESCRIPTION OF THE PREFERRED EMBODIMENT

While the present invention will be described more fully hereinafter with reference to the accompanying drawings, in which particular embodiments and methods are shown, it is to be understood from the outset that persons of ordinary skill in the art may modify the invention herein described while achieving the functions and results of this invention. Accordingly, the description which follows is to be understood as illustrative and exemplary of specific embodiments within the broad scope of the present invention and not as limiting the scope of the invention. In the following descriptions, like numbers refer to similar features or like elements throughout.

Figure 1:
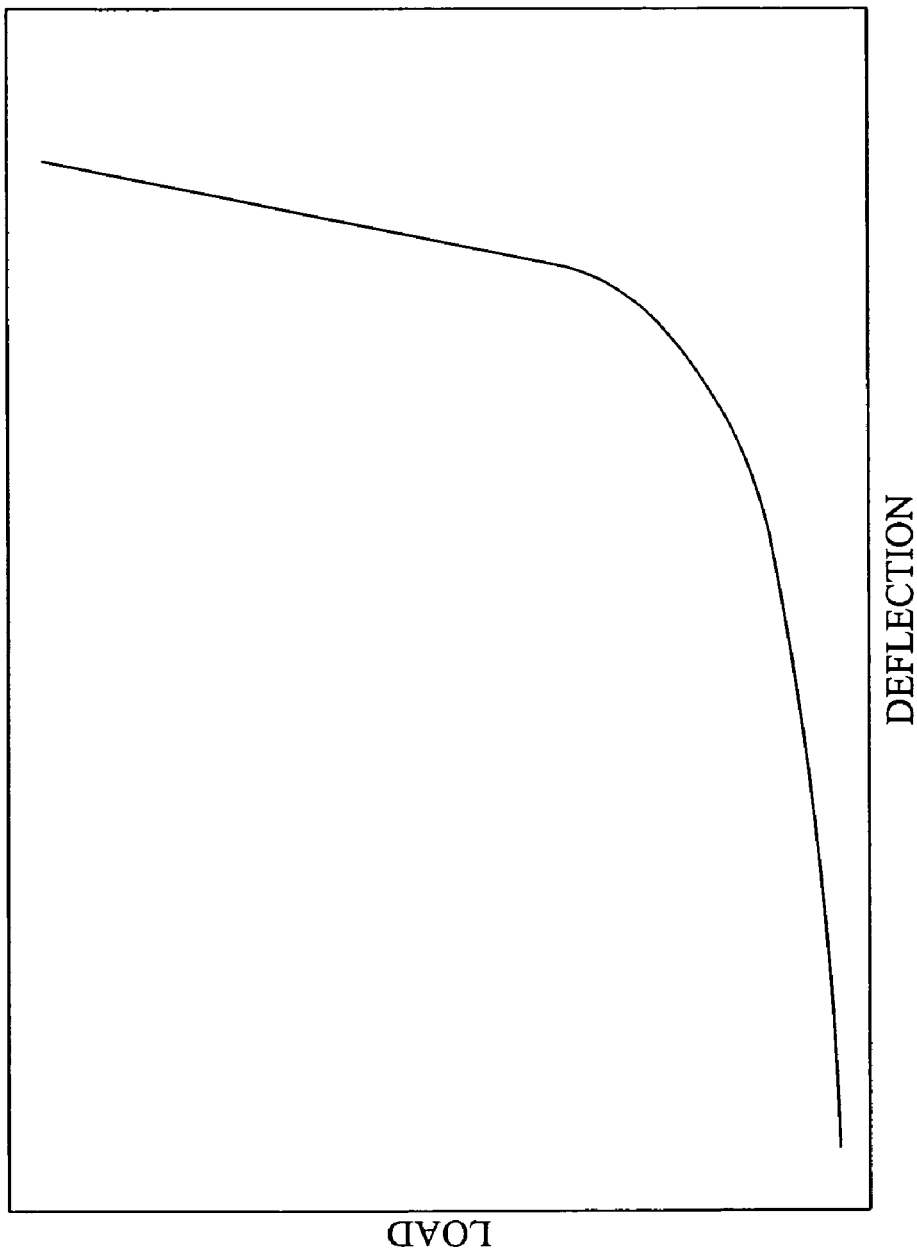
FIG. 1 is a graph showing the typical nonlinear response to load of human spine motion segments.

A successful intervertebral disc prosthesis should restore and preserve physiologic function of a normal spinal motion segment. FIG. 1 is a graph of the response of the normal human disc to load. The nonlinear response of the motion segment is a function not only of the disc, but of the facet joints and ligaments. Facet joint function and ligamentous structures may be compromised and unable to provide load sharing as in a normal motion segment. The nonlinear response of spine motion segment to load shown in FIG. 1 is a typical curve shape in compression, shear, torsion, and bending.

Figure 2:
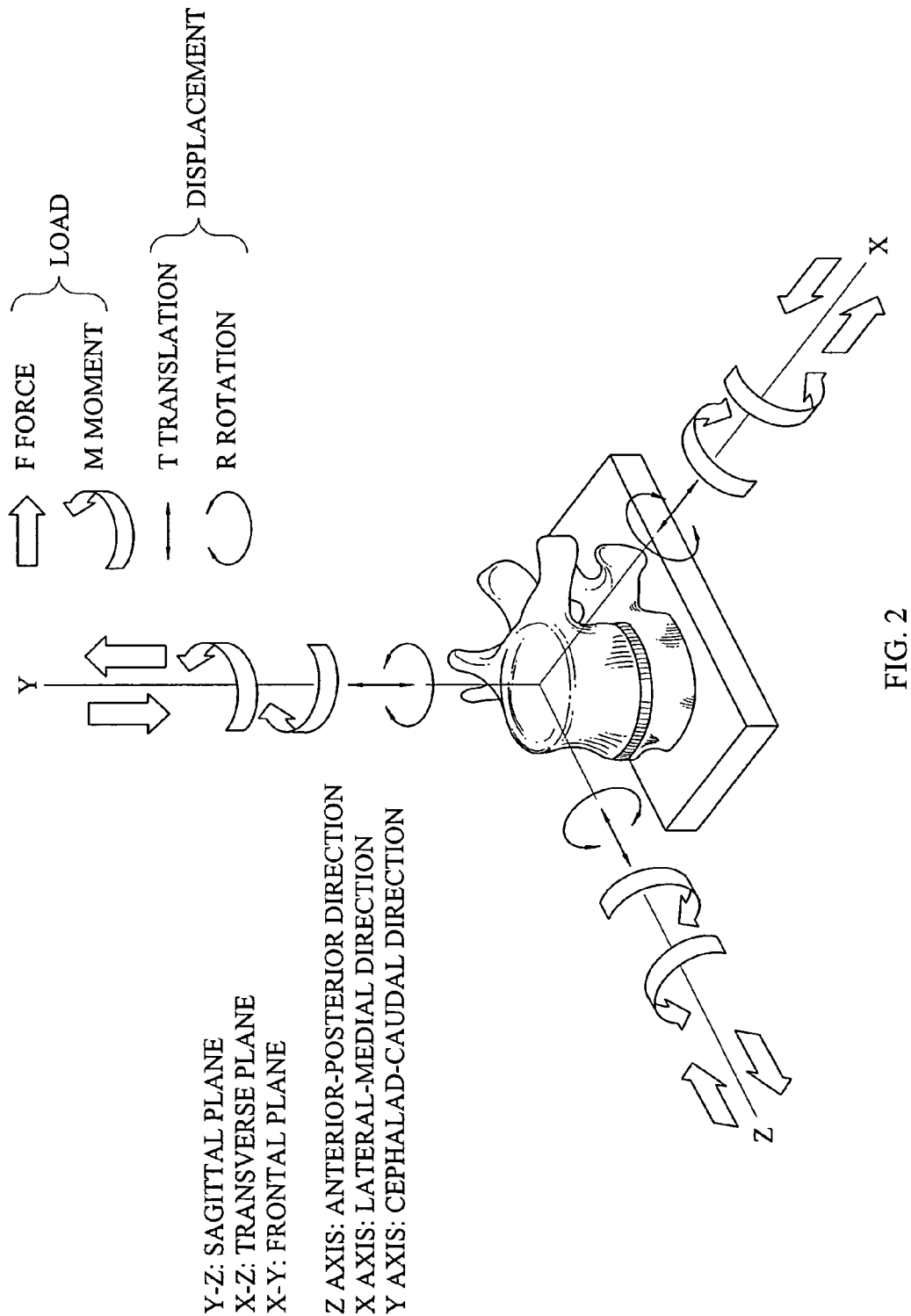
FIG. 2 is a diagram showing a reference coordinate system for a functional spinal unit to be used herein.

FIG. 2 is a perspective view of a reference intervertebral disc coordinate system that will be used throughout this discussion for ease of reference. The figure shows typical loads (forces and moments) and typical displacements (translation and rotation) that can occur in each of the three mutually orthogonal directions. The load-deflection curve shape of FIG. 1 is similar in all three directions for a normal disc. Like that of a normal disc, a disc 10 of the present invention provides a nonlinear response to torsion, shear, and compressive loads.

Figure 3:
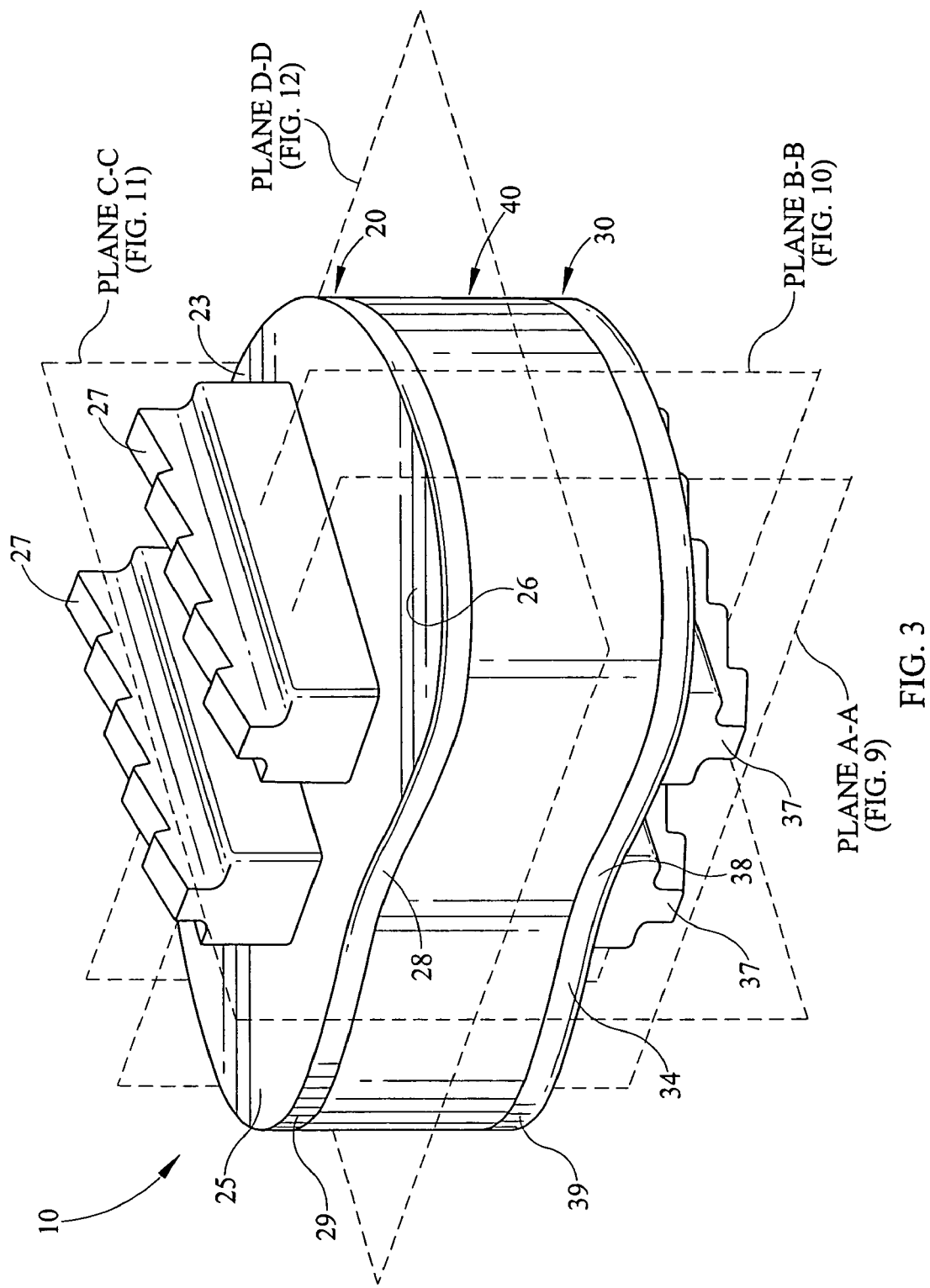
FIG. 3 is a posterior perspective view of a first embodiment of an artificial disc of the present invention.

Referring now to FIG. 3, the disc 10 comprises a first or upper endplate 20, a second or lower endplate 30, and a visco-elastic cushion 40 interposed between and adhered to the two endplates. The visco-elastic cushion 40 may comprise a variety of material, such as, for example, a polymeric material. The upper and lower plates 20, 30 are substantially symmetrical about an anterior-posterior horizontally extending plane (a transverse plane shown in FIG. 2), as well as about a sagittal plane (FIG. 2). The terms "upper" and "lower" are used herein only for illustration purposes with reference to the orientation of the disc 10 when it is implanted in the human body between two adjacent vertebrae V1 and V2 (defined as the cephalad-caudal direction in FIG. 2). Indeed, the upper plate is more generally described as a first plate and the lower plate is more generally described as a second plate.

The upper endplate 20 is rigid and is preferably made from a biocompatible material such as stainless steel, titanium, titanium alloys (such as Ti6Al4V), composite materials, and the like. The most preferred material is cobalt chrome molybdenum (CoCrMo or "CCM") comprising approximately 66% Co, 28% Cr, and 6% Mo by weight.

The upper endplate 20 has an upper surface 21 and a lower surface 22 and an anterior portion 23 and a posterior portion 24. Upper surface 21 and lower surface 22 are generally parallel. The anterior portion 23 is the portion of the upper endplate 20 that is disposed anteriorly in the spine when the disc 10 is implanted. Likewise, the posterior portion 24 is the portion of the upper endplate 20 that is disposed posteriorly in the spine when the disc 10 is implanted. The upper endplate 20 has an external surface 29 therearound that preferably defines a generally "D" shape. In one embodiment of the invention, the posterior portion 24 of the external surface 29 has a concavity 28 therein that defines posterior lobes 25, 26 projecting from the posterior portion 24 (see FIGS. 3, 4, 5, 12, 14, and 15). One or more appurtenance 27 may be optionally affixed to the upper surface 21 to facilitate attachment.

The upper endplate 20 likewise may comprise an upper subplate 200 (see FIG. 15) that can be formed monolithic with the upper endplate 20 or as a separate component affixed thereto subsequent to manufacture. Alternatively, the structures that comprise the upper subplate 200 may simply be included in the upper endplate 20. The remainder of this description will discuss structure related to subplate 200, but it should be recognized that the description applies equally to discs having no separate subplate. The subplate 200 further comprises an upper surface 210 and a lower surface 220 and an anterior portion 230 and a posterior portion 240. A first projection 270 optionally may depend from the lower surface 220 of the subplate 200 to act as part of a compression stop, as will be described below. The upper subplate 200 also has a plurality of openings 271 therethrough for receiving one or more motion-limiting members 80 (described below). Preferably, the upper subplate 200 includes two openings 271, one disposed posteriorly and slightly to the left (in the medial-lateral plane) of the first projection 270 and another disposed posteriorly and slightly to the right (in the medial-lateral plane) of the first projection 270 (assuming the center of rotation is at the geometric center of the disc). The openings 271 further comprise a bearing surface 272 for interacting with the motion-limiting members 80 or a split ring assembly 400 (described below). The bearing surface 272 is preferably a tapered opening having a larger diameter at the upper surface 210 than at the lower surface 220. The taper can be linear or nonlinear, including conic sections, parabolic sections, spherical sections, and so forth, to name only a few examples.

The first projection 270 preferably extends from said lower surface 220 a height of approximately 1 mm to approximately 3 mm. Many shapes are possible for the first projection 270, and indeed multiple projections, or no projections, are contemplated as well. In the preferred embodiment, the first projection 270 takes the form of a substantially cylindrical section having a slight radius on its terminal end of approximately 2 mm to approximately 15 mm, preferably approximately 8 mm to approximately 12 mm.

In like manner, the disc 10 further comprises a lower endplate 30. The lower endplate 30 is rigid and is preferably made from a biocompatible material such as stainless steel, titanium, titanium alloys (such as Ti6Al4V), composite materials, and the like. The preferred material is cobalt chrome molybdenum (CCM) comprising approximately 66% Co, 28% Cr, and 6% Mo by weight, respectively.

The lower endplate 30 has an upper surface 31 and a lower surface 32 and an anterior portion 33 and a posterior portion 34. Upper surface 31 and lower surface 32 are generally parallel. The anterior portion 33 is the portion of the lower endplate 30 that is disposed anteriorly in the spine when the disc 10 is implanted. Likewise, the posterior portion 34 is the portion of the lower endplate 30 that is disposed posteriorly in the spine when the disc 10 is implanted. The lower endplate 30 has an external surface 39 therearound that preferably defines a generally "D" shape. In one embodiment of the invention, the posterior portion 34 of the external surface 39 has a concavity 38 therein that defines posterior lobes 35, 36 projecting from the posterior portion 34 (see FIGS. 3, 4, 5, 12, 14, and 15). One or more appurtenance 37 may be optionally affixed to the lower surface 32 to facilitate attachment.

Figure 8:
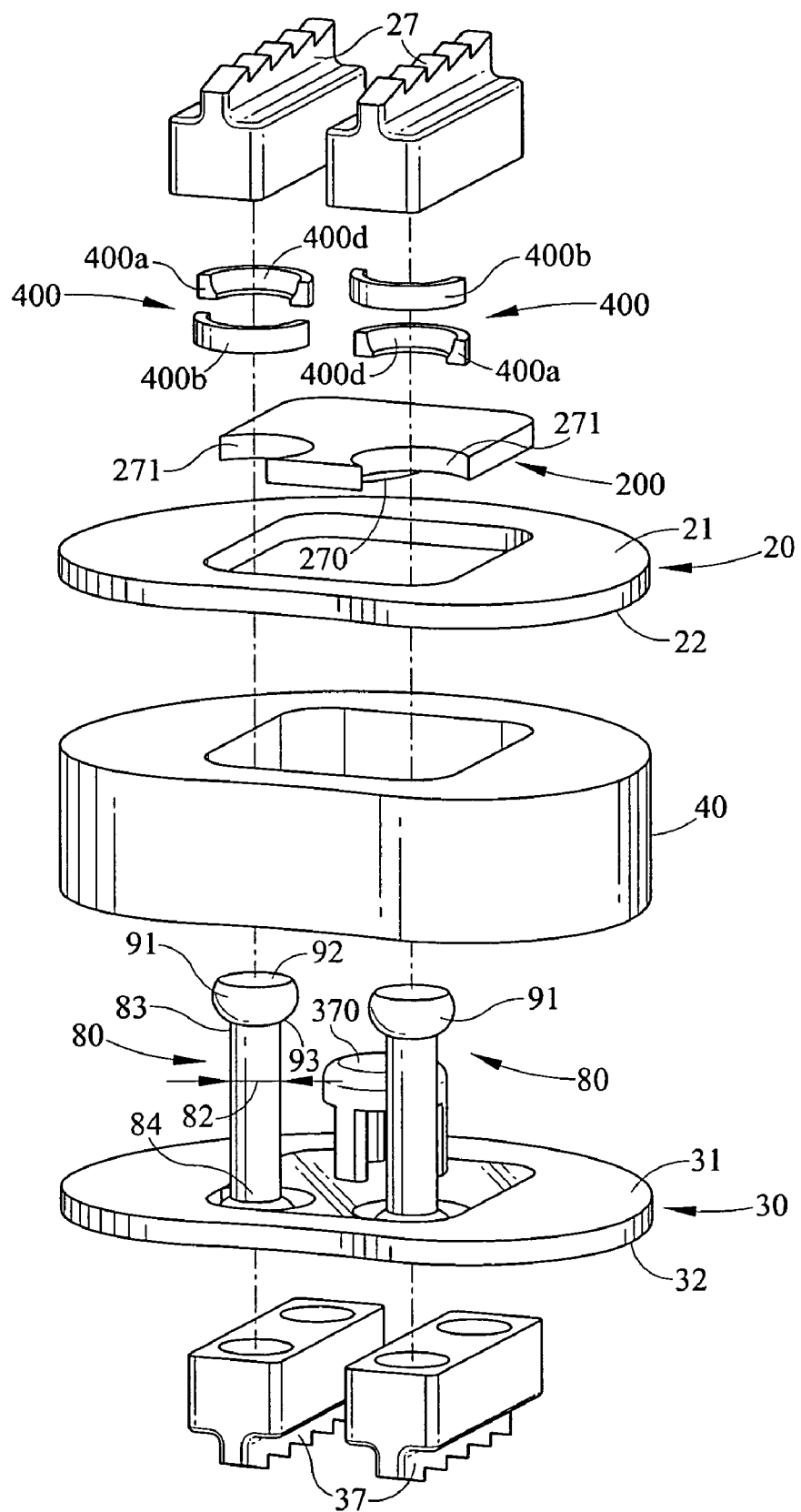
FIG. 8 is an exploded perspective view of the artificial disc shown in FIG. 3.
Figure 9:
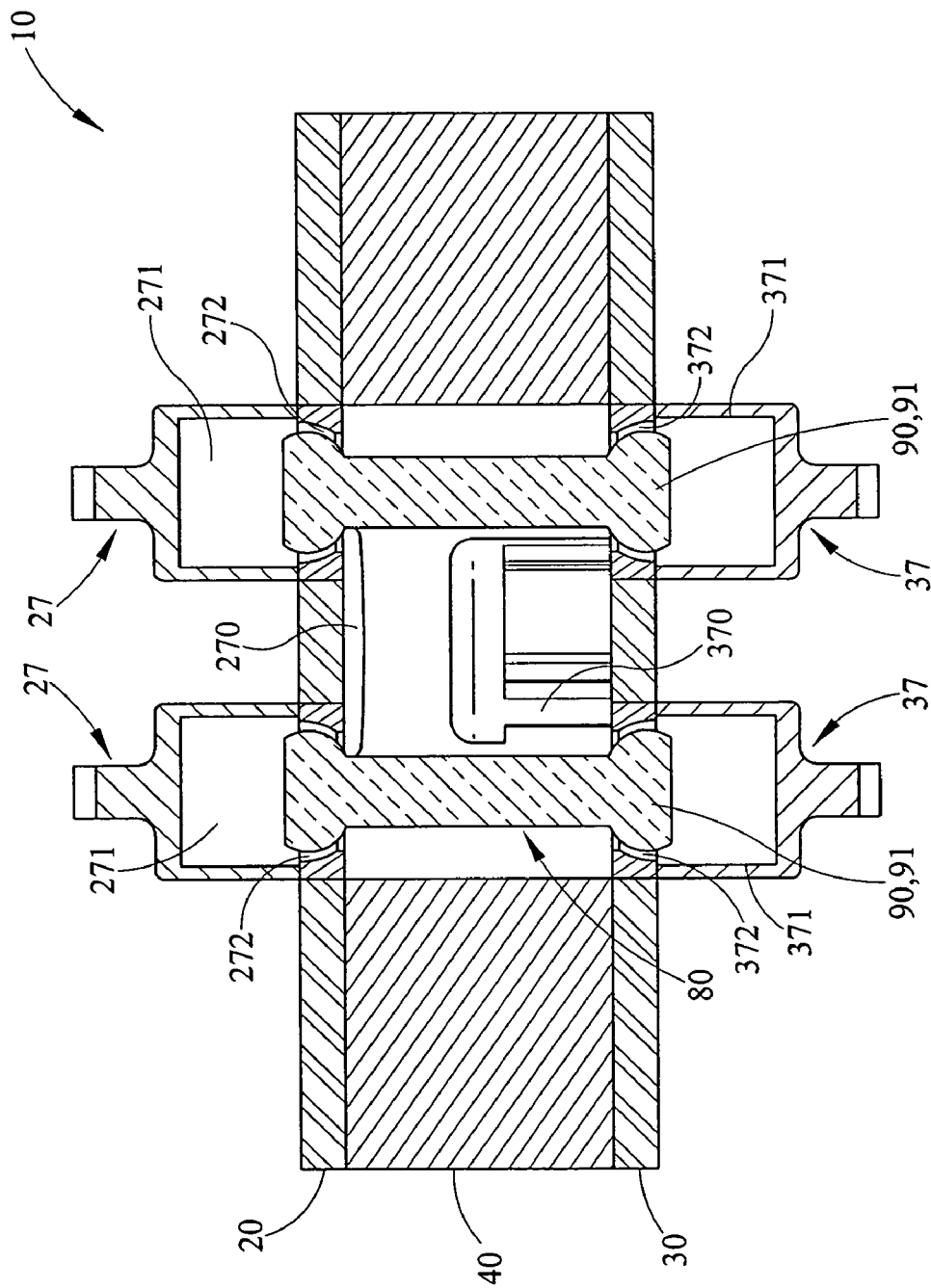
FIG. 9 is a section view taken along plane A-A in FIG. 3.
Figure 10:
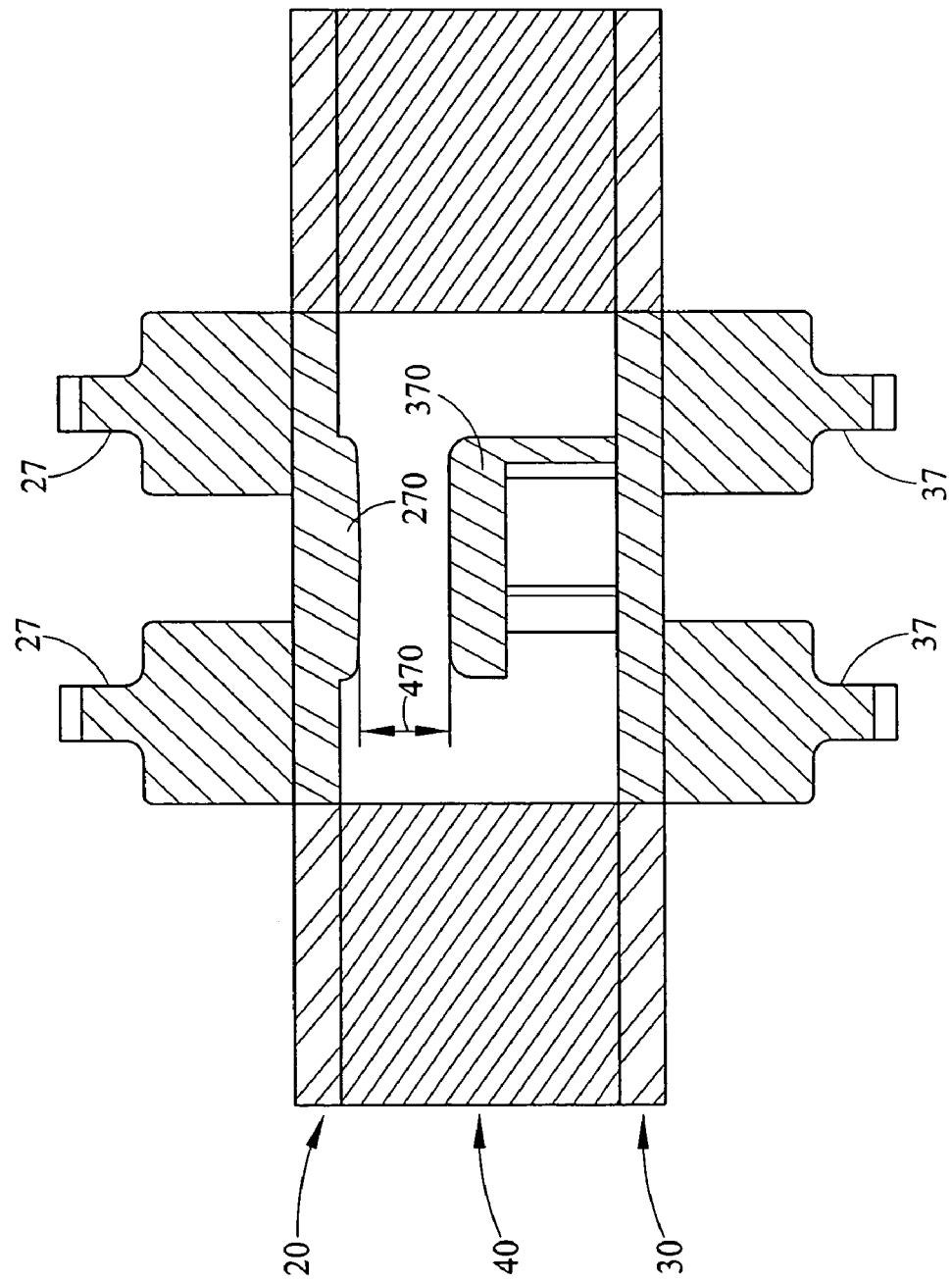
FIG. 10 is a section view taken along plane B-B in FIG. 3.
Figure 11:
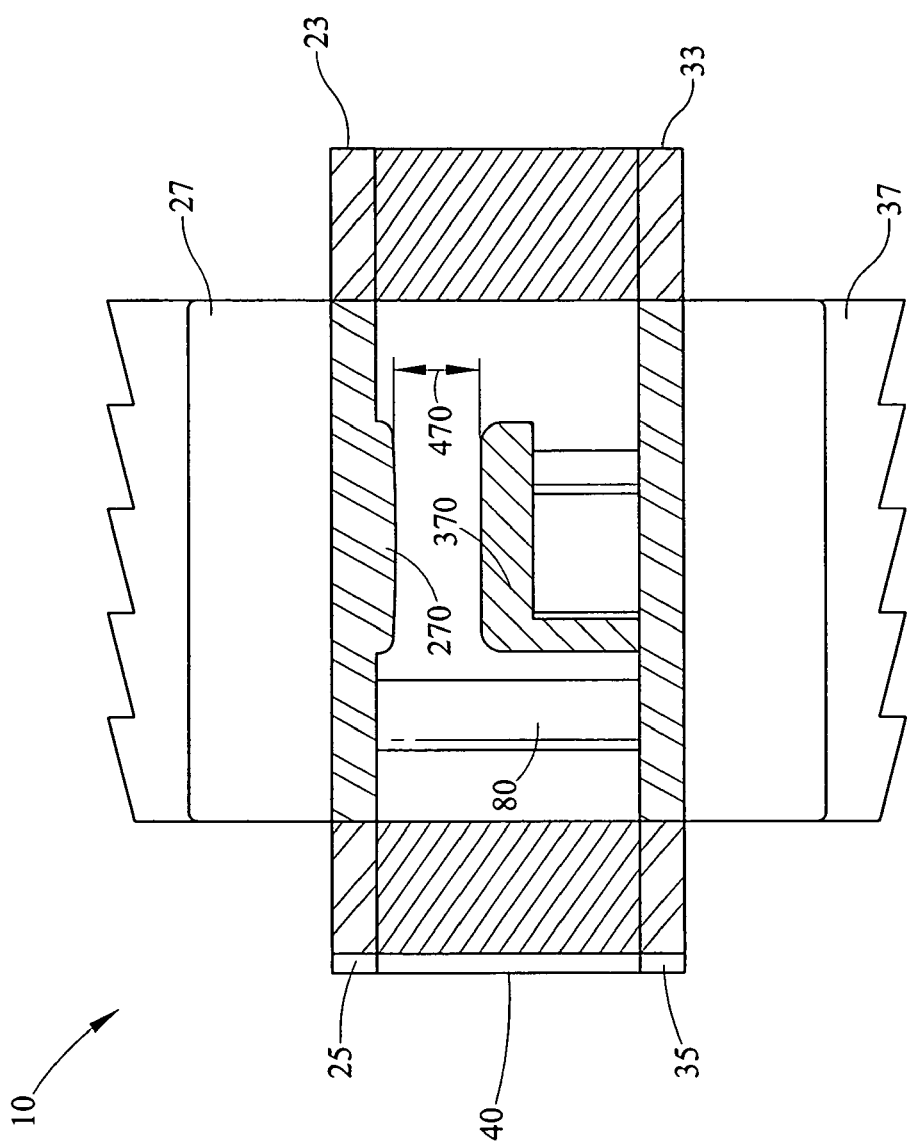
FIG. 11 is a section view taken along plane C-C in FIG. 3.
Figure 12:
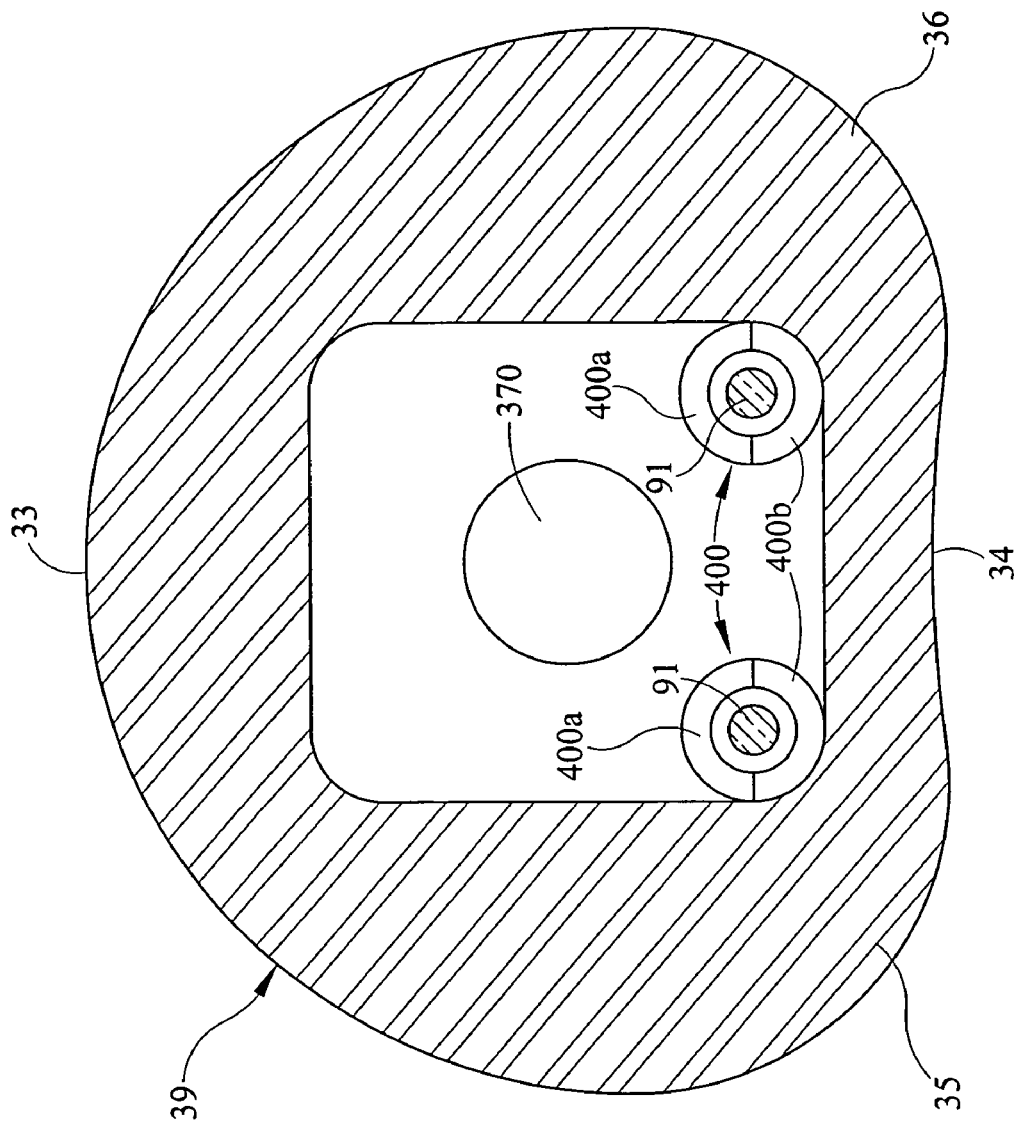
FIG. 12 is a section view taken along plane D-D in FIG. 3.
Figure 13:
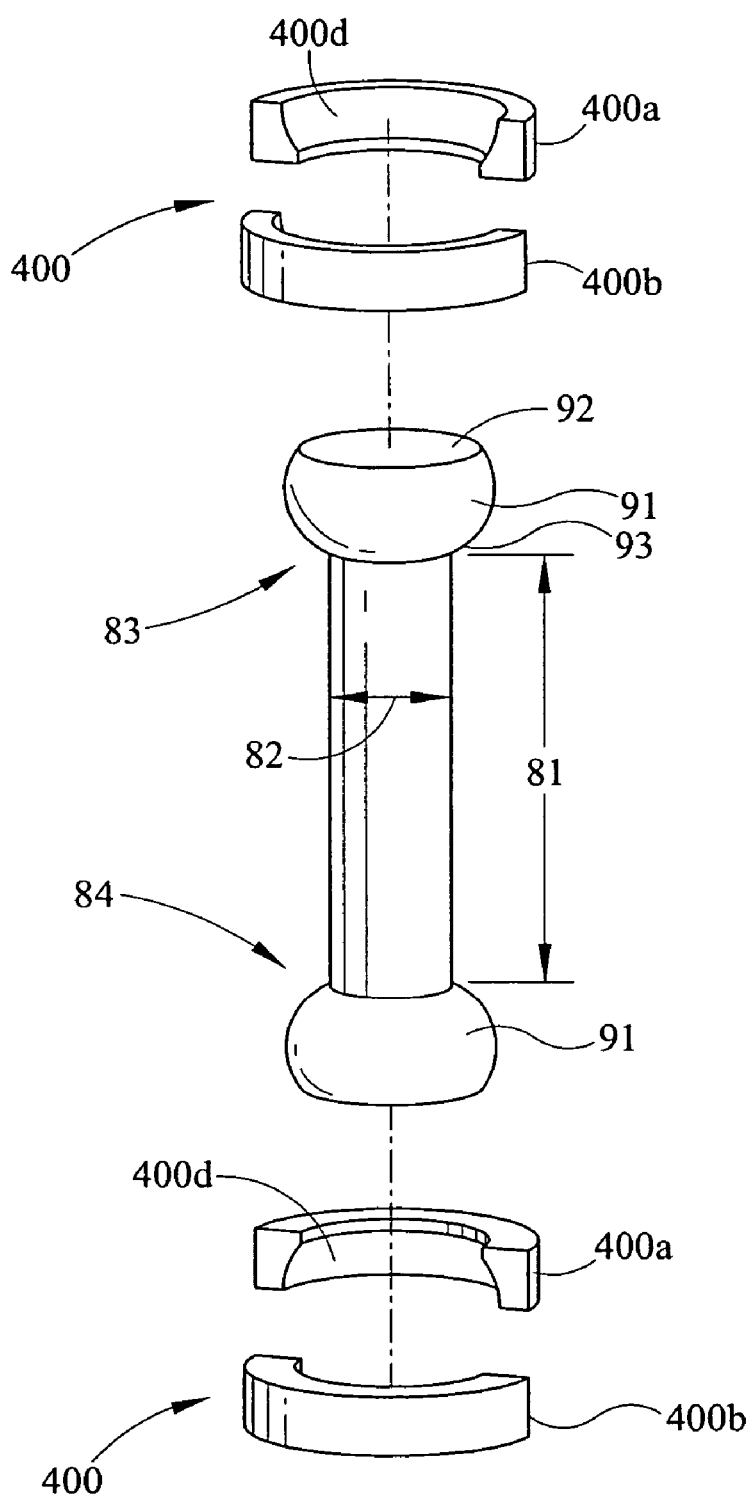
FIG. 13 is an exploded perspective view of an exemplary motion-limiting member of a first embodiment of the invention.
Figure 14:
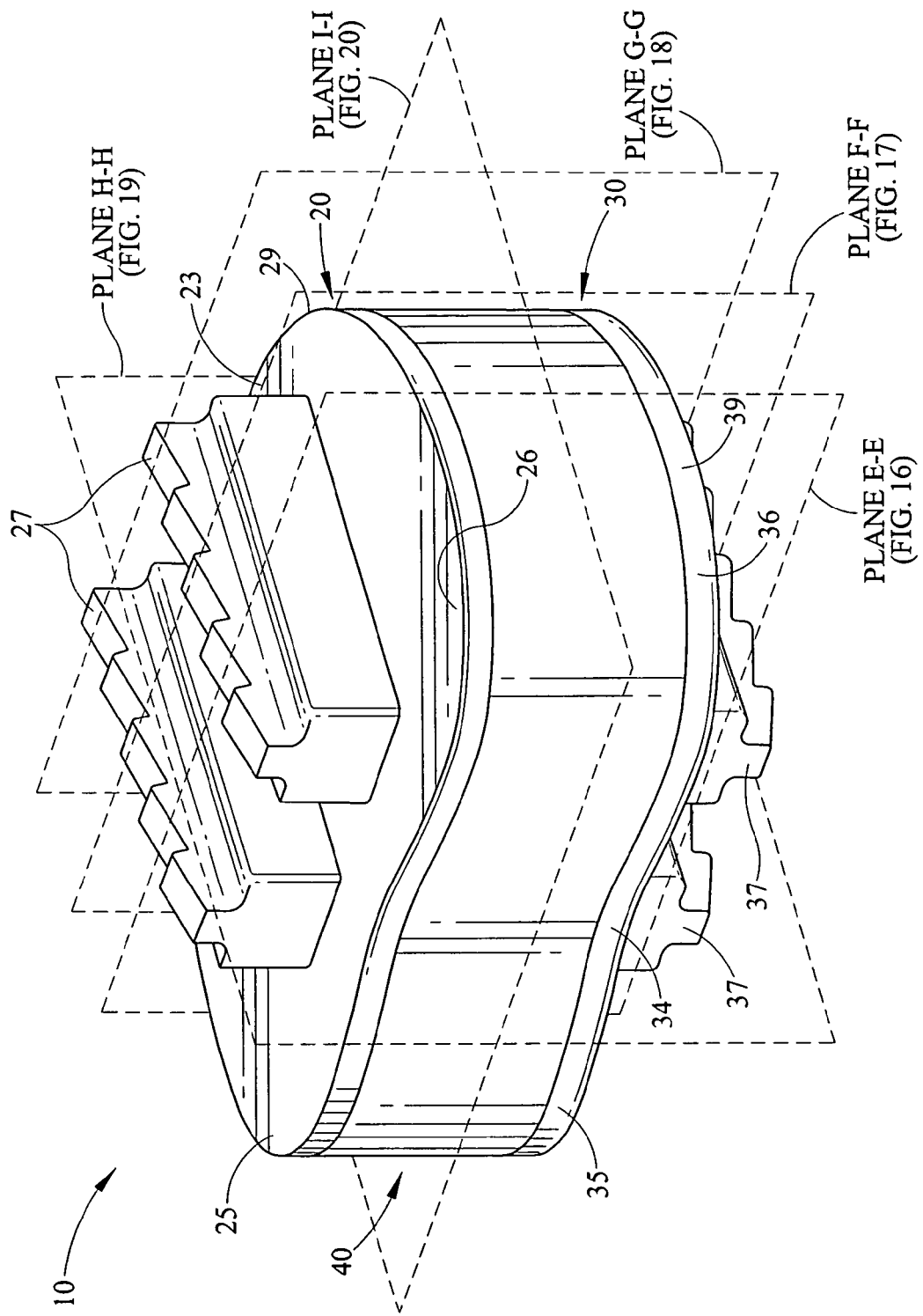
FIG. 14 is a perspective view of a second embodiment of an artificial disc of the present invention having four motion-limiting members therein.
Figure 15:
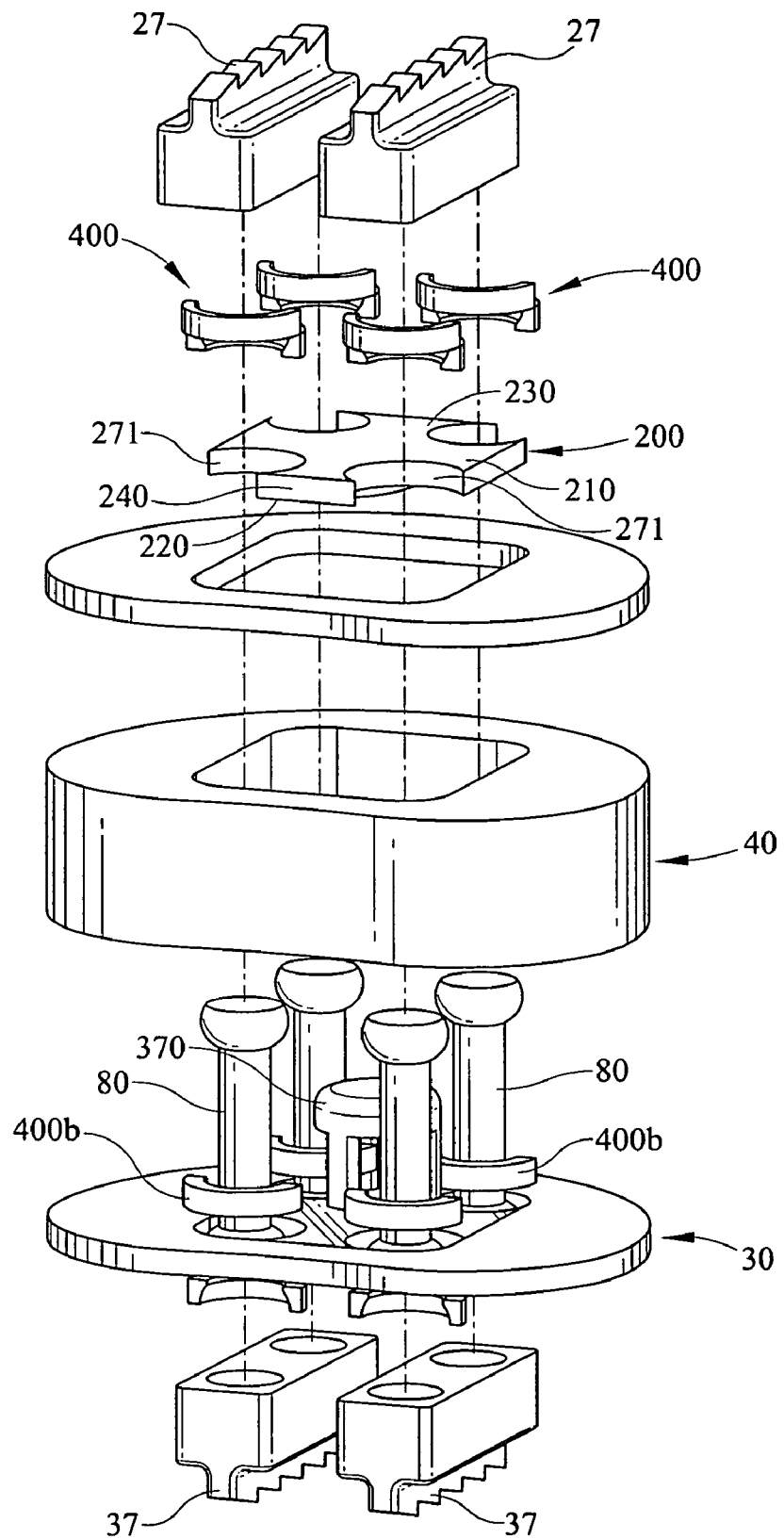
FIG. 15 is an exploded perspective view of the embodiment of the artificial disc of the present invention shown in FIG. 14.
Figure 16:
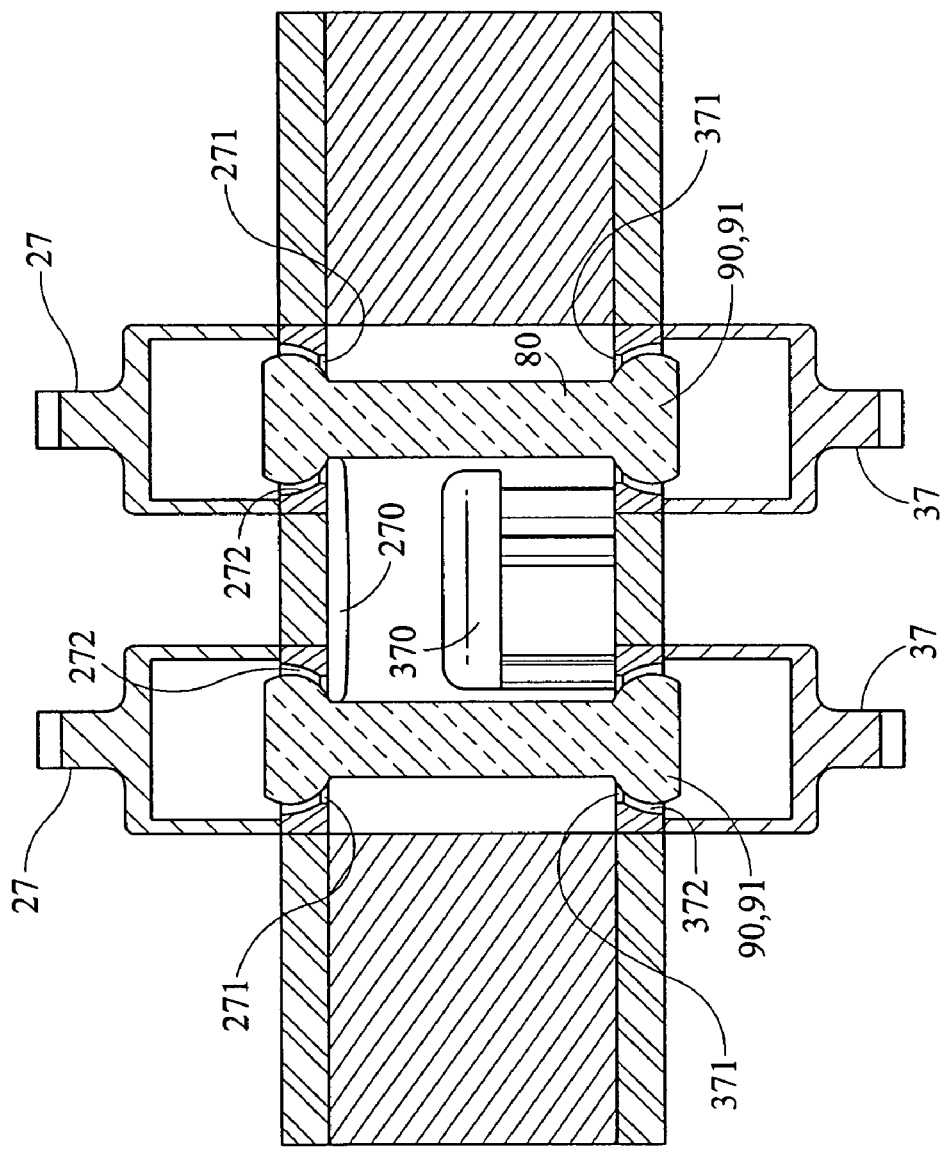
FIG. 16 is a section view taken along plane E-E in FIG. 14.
Figure 17:
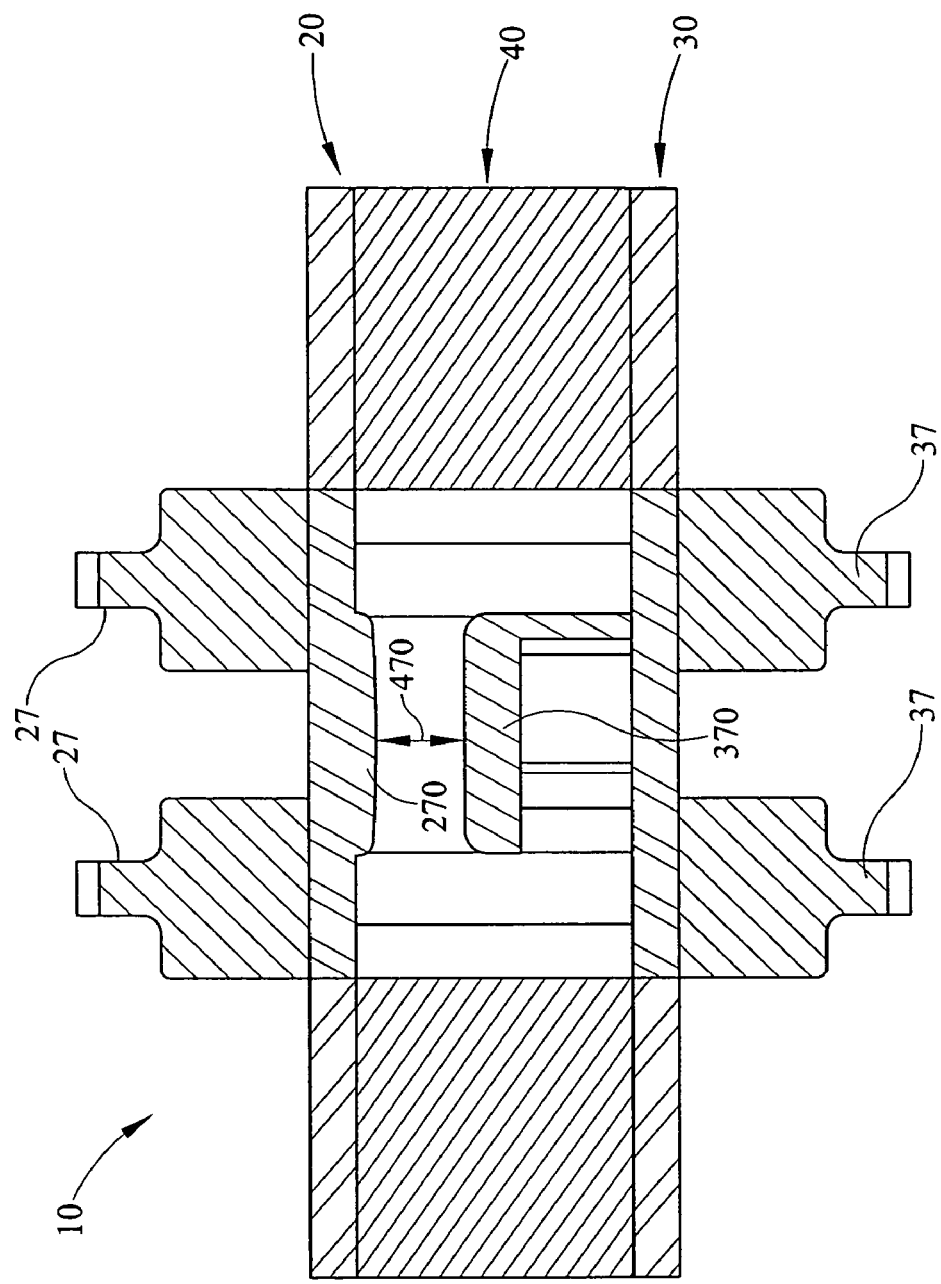
FIG. 17 is a section view taken along plane F-F in FIG. 14.
Figure 18:
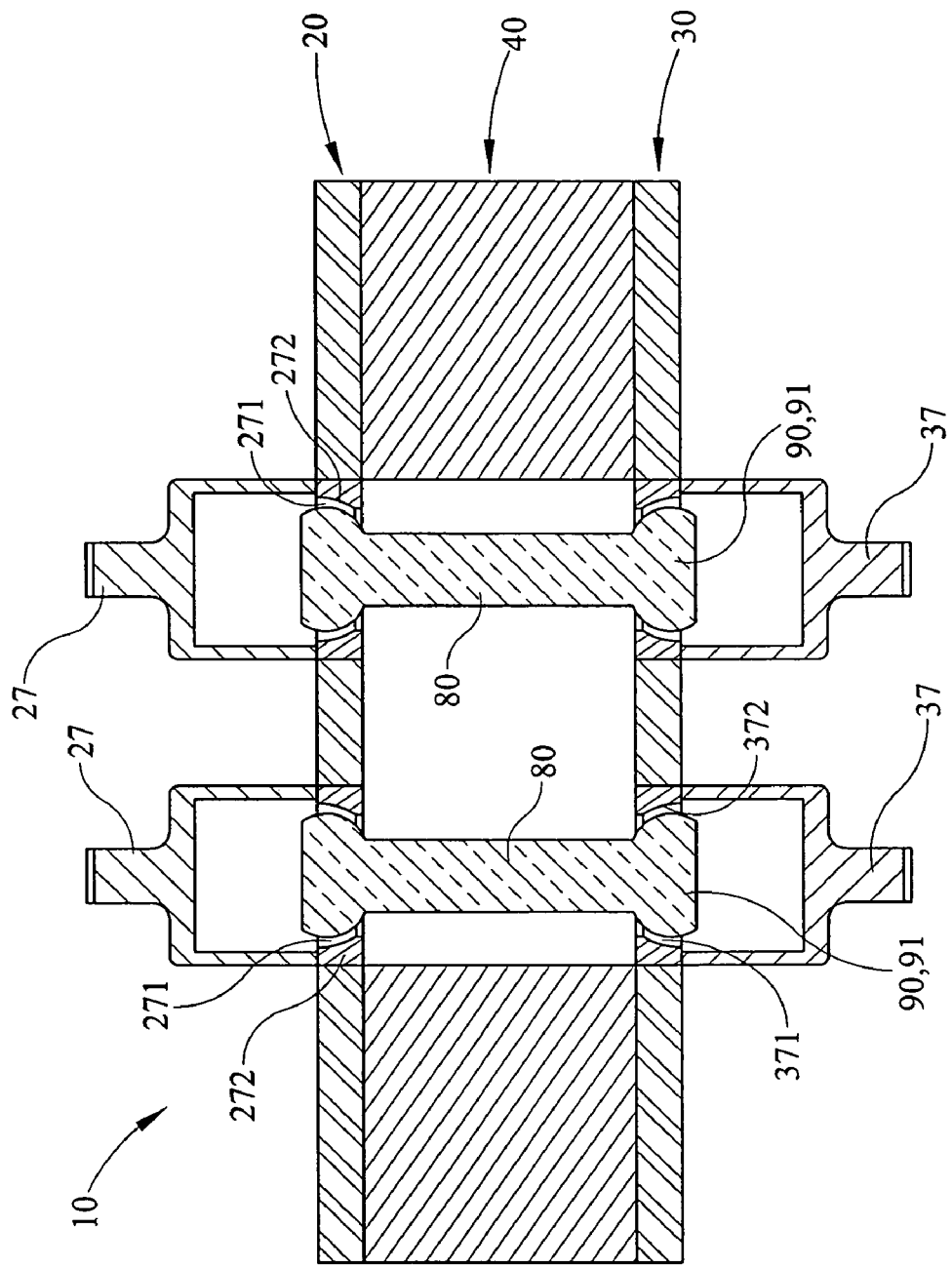
FIG. 18 is a section view taken along plane G-G in FIG. 14.
Figure 19:
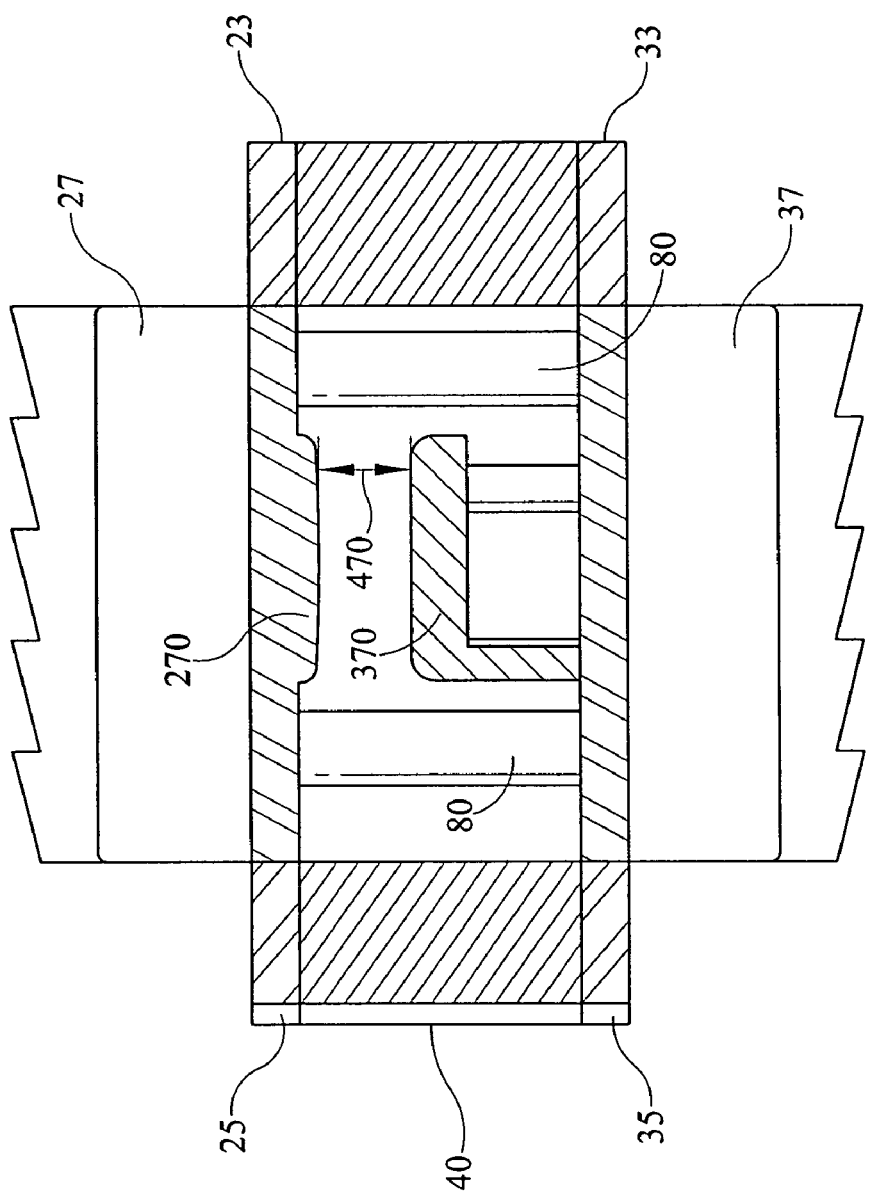
FIG. 19 is a section view taken along plane H-H in FIG. 14.
Figure 20:
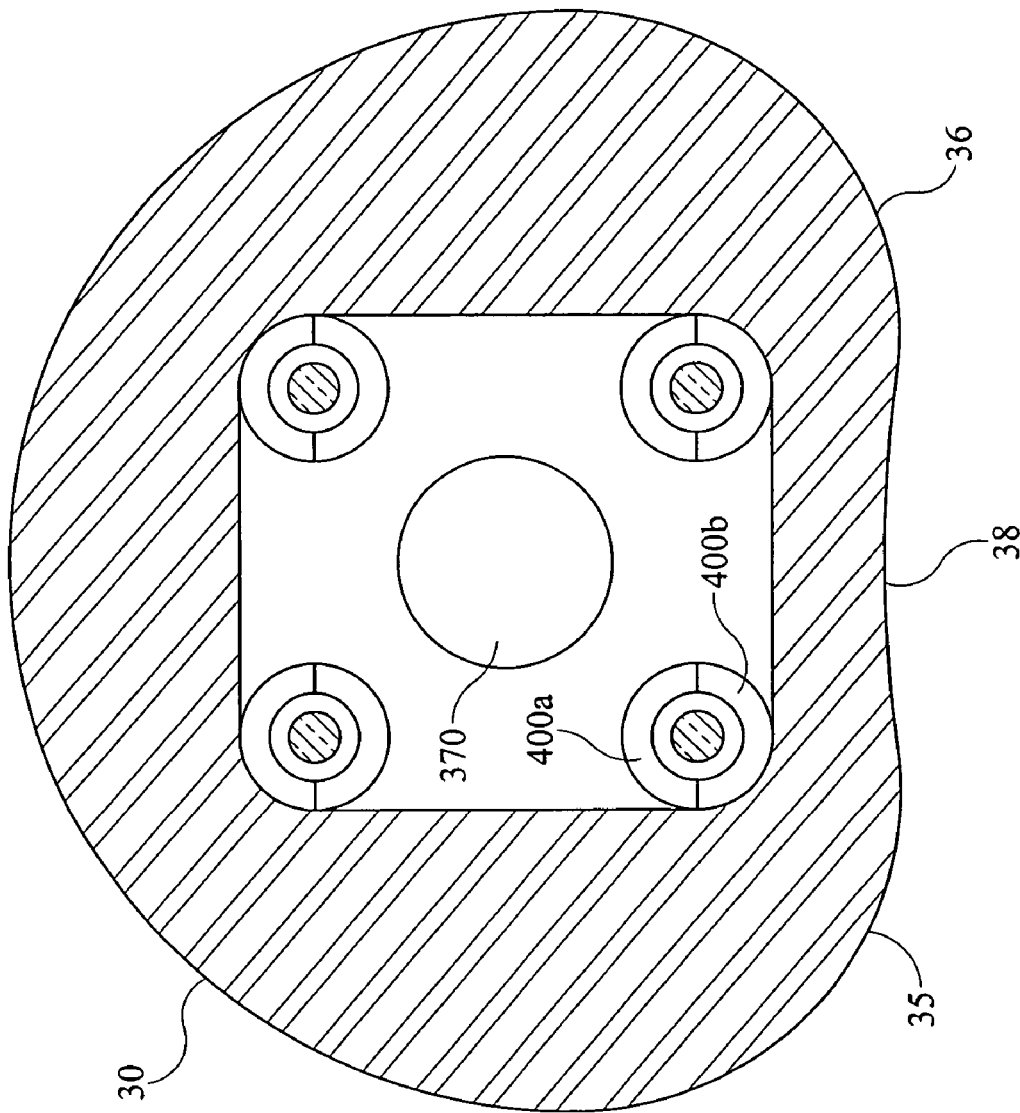
FIG. 20 is a section view taken along plane I-I in FIG. 14.

Although not preferred, it is possible that the lower endplate 30 may comprise a lower subplate 300 (see FIGS. 8 and 15) that can be formed monolithic with the lower endplate 30 or as a separate component affixed thereto subsequent to manufacture. The subplate 300 further comprises an upper surface 310 and a lower surface 320 and an anterior portion 330 and a posterior portion 340. A second projection 370 depends from the upper surface 310 of the subplate 300 to act as part of a compression stop, as will be described below. The lower subplate 300 also has a plurality of openings 371 therethrough, having bearing surfaces 372, for receiving one or more motion-limiting members 80 (described below). Preferably, the lower subplate 300 includes two openings 371, one disposed posteriorly and slightly to the left of the first projection 370 and another disposed posteriorly and slightly to the right of the first projection 370.

The second projection 370 preferably extends from said upper surface 310 a height of approximately 3 mm to approximately 6 mm. Preferably the second projection 370 is in substantial alignment with the first projection 270. Stated otherwise, the second projection 370 preferably will have its longitudinal axis aligned with or close to the longitudinal axis of the first projection 270. This is not mandatory, however. Indeed, the two projections 270, 370 may be offset from one another, it being more important that at least a portion of the projections 270, 370 overlap during contact therebetween. And, depending on the respective shapes of the projections 270, 370, the amount of offset may vary. Many shapes are possible for the second projection 370, including, but not limited to, all regular polygonal shapes. Additionally, the projections 270, 370 may take the form of partial polygons (for example, a half cylinder or a partial elliptical cylinder, to name but a few). In the preferred embodiment, the second projection 370 takes the form of a cylindrical platform having a diameter of approximately 6 mm to 10 mm, and more particularly, approximately 7 mm to approximately 9 mm.

Referring now to FIGS. 8, 9, 12 and 13, a motion-limiting member 80 typically resides within each opening 271, 371. Each motion-limiting member 80 has a length 81 and a diameter 82, and a first end 83 and a second end 84. At each end 83, 84 is an enlarged portion 90. The motion-limiting members 80 link the upper endplate 20 to the lower endplate 30 and assist in handling the loads associated with flexion, as will be described below.

The motion-limiting members 80 can be any of several longitudinal rod-like members, both rigid and semi-rigid, including solid metallic bars or rods of varying cross-sections, and wire. If wire is used as the motion-limiting member 80, the motion-limiting members 80 typically have diameters of approximately 0.038 inches to approximately 0.080 inches. However, the number of motion-limiting members 80 used plays a role in determining the diameter of each motion-limiting member 80. In the preferred embodiment, there are two motion-limiting members 80 that are braided metal wires, preferably a braided stainless steel wire having a diameter of approximately 0.062 inches and a rated tensile strength of approximately 320 pounds. More specifically, the motion-limiting members 80 can be of any material described above, but are preferably cables of 316L stainless, MP35N, Haynes 25. In alternative, though less preferred, embodiments where substantially more numerous motion-limiting members 80 are used (for example ten to twenty), the diameters can be significantly smaller.

The enlarged portion 90 at each end 83, 84 is typically a spherically-shaped structure, or ball 91, that is affixed to the motion-limiting member 80. Balls 91 are preferably of the same material as the motion-limiting members 80. The ball 91 has an upper surface 92 and a lower surface 93. Preferably, ball 91 is preformed onto the motion-limiting member 80. However, methods of fixation are also varied and include welding, both during formation of the ball 91 at the first end 83 and during assembly of the ball 91 at the second end 84; as well as crimping on a ball 91. The balls 91 are preferably hemispheres wherein the lower surface 93 engages the bearing surface 272 of the plates 20, 30 and/or the subplate 200, 300. The upper surface 92 of the ball 91 provides little to no advantage and merely takes up space. As a result, the upper surface 92 is preferably flat or very low-profile so as to take up a minimal amount of space. The appurtenances 27, 37 on the upper and lower endplates 20, 30, respectively, may be used to cover a portion of the enlarged portions 91. In some embodiments, however, the inside surface 400d of the split ring assembly (described below) can be used to effectively shorten the length of the motion-limiting member 80 such that no part of the enlarged portion 91 extends beyond the upper surface 21 of the upper endplate or the lower surface 32 of the lower endplate 30.

In the preferred embodiment, a split ring assembly 400, as shown in FIGS. 8, 13, 15, and 24, fits into the openings 271 of the upper subplate 200 and into openings 371 of the lower subplate 300. The split ring assembly 400 comprises a first half 400a and a second half 400a. When the two halves 400a, 400b of the split ring assembly 400 are combined, they form a ring-shaped member having a port 400c defined by a periphery 400e. The split ring assembly 400 includes an inside surface 400d that serves as a bearing surface against which the balls 91 can articulate, resulting in a mini-ball and socket joint. The diameter of port 400c is smaller than that of the ball 91. Thus, when assembling the artificial disc prosthesis, the motion-limiting member 80 is inserted into the opening 271 of the upper subplate 200 at the first end 83 and into the opening 371 of the lower subplate 300 at the second 84. The first half 400a of the split ring assembly 400 is then inserted into the opening 271 underneath the ball 91 at the first end 83 of the motion-limiting member 80. Then, the second half 400b of the split ring assembly 400 is inserted into the opening 271 of the upper subplate 200 underneath the ball 91 at the first end 83 of the motion-limiting member 80, completing the split ring assembly 400 in the upper subplate 200. Since the diameter of the port 400c in the split ring assembly is smaller than that of the ball 91 at the first end 83 of the motion-limiting member 80, the motion-limiting member 80 is prevented from slipping through the opening 271 of the upper subplate 270.

In the same manner, a split ring assembly 400 is inserted into the opening 371 of the lower subplate 300 above the ball 91 at the second end 84 of the motion-limiting member 80 in order to prevent the motion-limiting member 80 from slipping through the opening 370 of the lower subplate 300. Once the split ring assemblies 400 are in place, they may be welded or permanently affixed by some other means known in the art to the upper and lower subplate assemblies 200, 300. The split ring assembly 400 includes an inside surface 400d that serves as a bearing surface against which the balls 91 can articulate, resulting in a mini-ball and socket joint, thus minimizing the bending of the motion-limiting member 80 and extending fatigue life.

In another embodiment, the split ring assembly 400 is not present, and the balls 91 are not preformed onto the motion-limiting members 80. Instead the balls 91 are fixed onto the motion-limiting members 80 through some other means such as welding or crimping, as discussed above. However, welding the ends of the motion-limiting members 80 into balls 91 can lower the strength of the motion-limiting members 80 by 10 to 15 percent. In this embodiment, the diameter of ball 91 can be controlled during welding, ranging in size from approximately slightly larger than the diameter of the motion-limiting member 80 up to a maximum diameter of approximately two times the motion-limiting member diameter. In embodiments using other attachment methods, other diameters are possible. Since no split ring assembly 400 is present in this embodiment to prevent the motion-limiting members 80 from slipping out of the openings 271, 371 of the upper and lower subplates 200, 300, respectively, it is necessary that the diameter of the balls 91 be larger than the diameter of the opening 271 at the lower surface 220 of the upper subplate 200 and the opening 371 at the upper surface 310 of the lower subplate 300.

In the embodiments containing no split ring assembly, the balls 91 at the first end 83 and the second end 84 mate with the bearing surface 272 of the openings 271 in each endplate 20, 30 and/or subplate 200, 300. As a result, each union of ball 91 and bearing surface 272 results in a mini-ball and socket joint that allows articulation of the ball 91 and motion-limiting member 80 within the opening 271, thus limiting bending of the motion-limiting member 80, thereby extending fatigue life.

The disc 10 of the preferred embodiment provides motion-limiting features in compression and bending, thereby behaving in vivo in a fashion more similar to a natural spinal disc. The first projection 270 and the second projection 370, by way of the predetermined gap 470 therebetween (see FIGS. 9, 10, 11, 16, 17, and 19), provide a compression stop preventing movement between the upper and lower plates 20, 30 in a magnitude greater than a predetermined amount. Varying limits of movement may be set, depending on the type and location of the disc 10 in the body. In the preferred embodiment, the gap 470 between the first and second projections 270, 370 is approximately 1 to 2 millimeters. Elastomers that can handle excessive compressive loadings may be able to accommodate a gap greater than 2 millimeters. Once a compressive load is applied to the disc 10, the visco-elastic cushion 40 absorbs the compression in a visco-elastic fashion according to design properties of the elastomer. Upon absorbing the compressive loads in amounts sufficient to cause relative movement between the upper endplate 20 and the lower endplate 30 in an amount equal to the gap 470, the first and second projections 270, 370 then come into contact and prevent further compressive loads from being applied to the elastomer. It is expected that the stop mechanism will only be activated during the most strenuous of activities of the patient.

Figure 21:
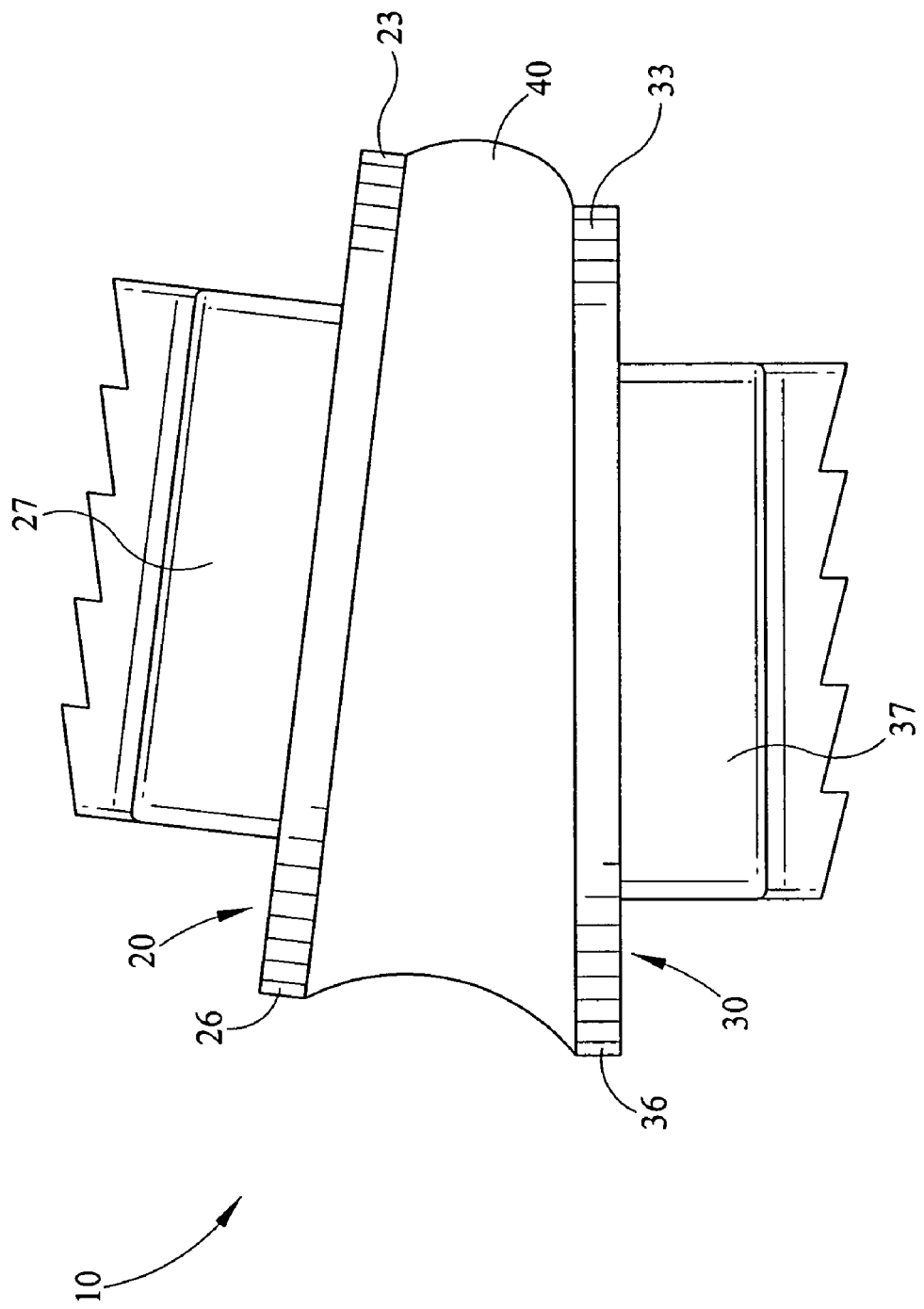
FIG. 21 is a side elevation view of a disc according to a first embodiment of the invention showing the disc in normal bending mode.
Figure 23:
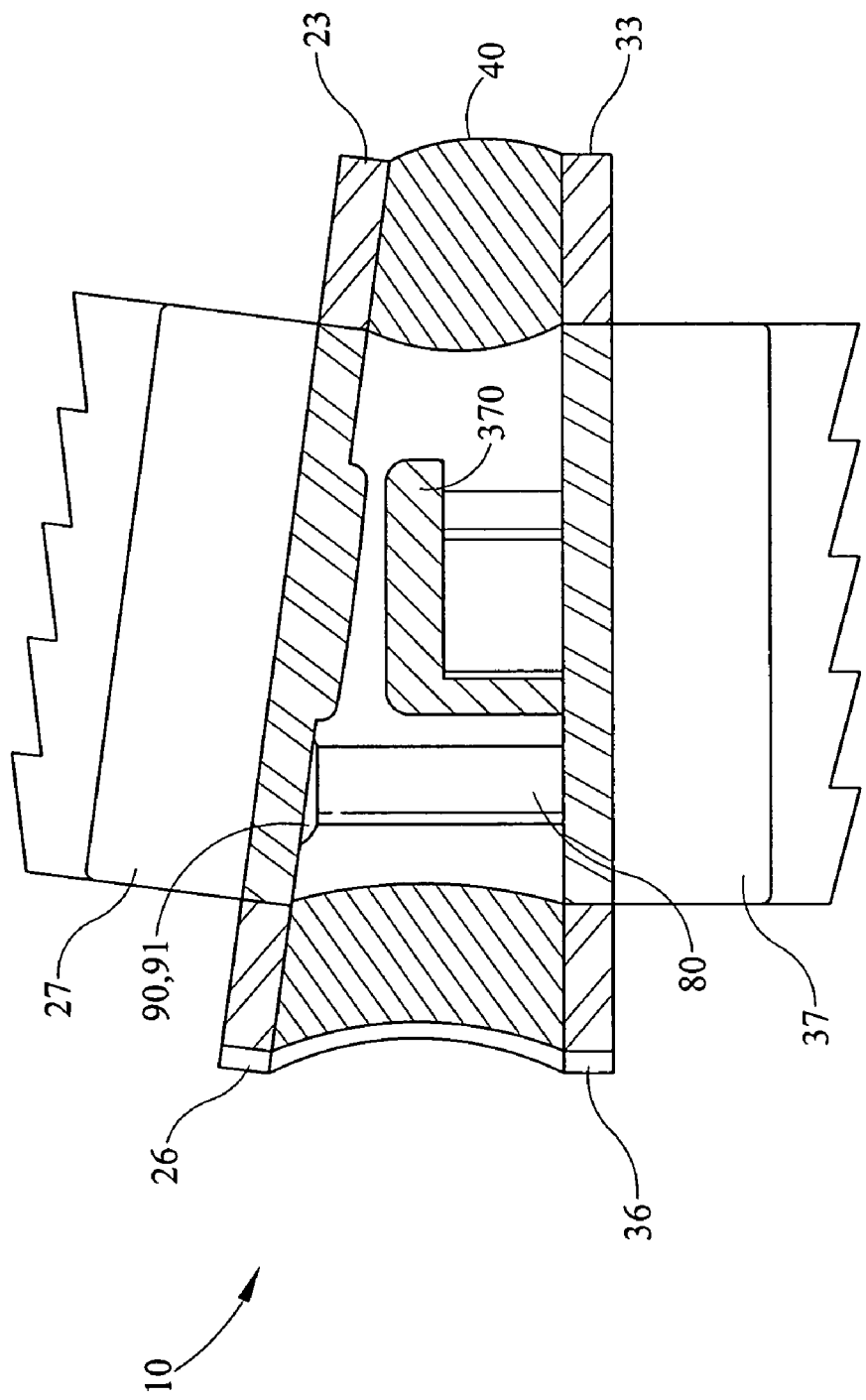
FIG. 23 is a side section view of the disc shown in FIG. 21 in normal bending mode.
Figure 24:
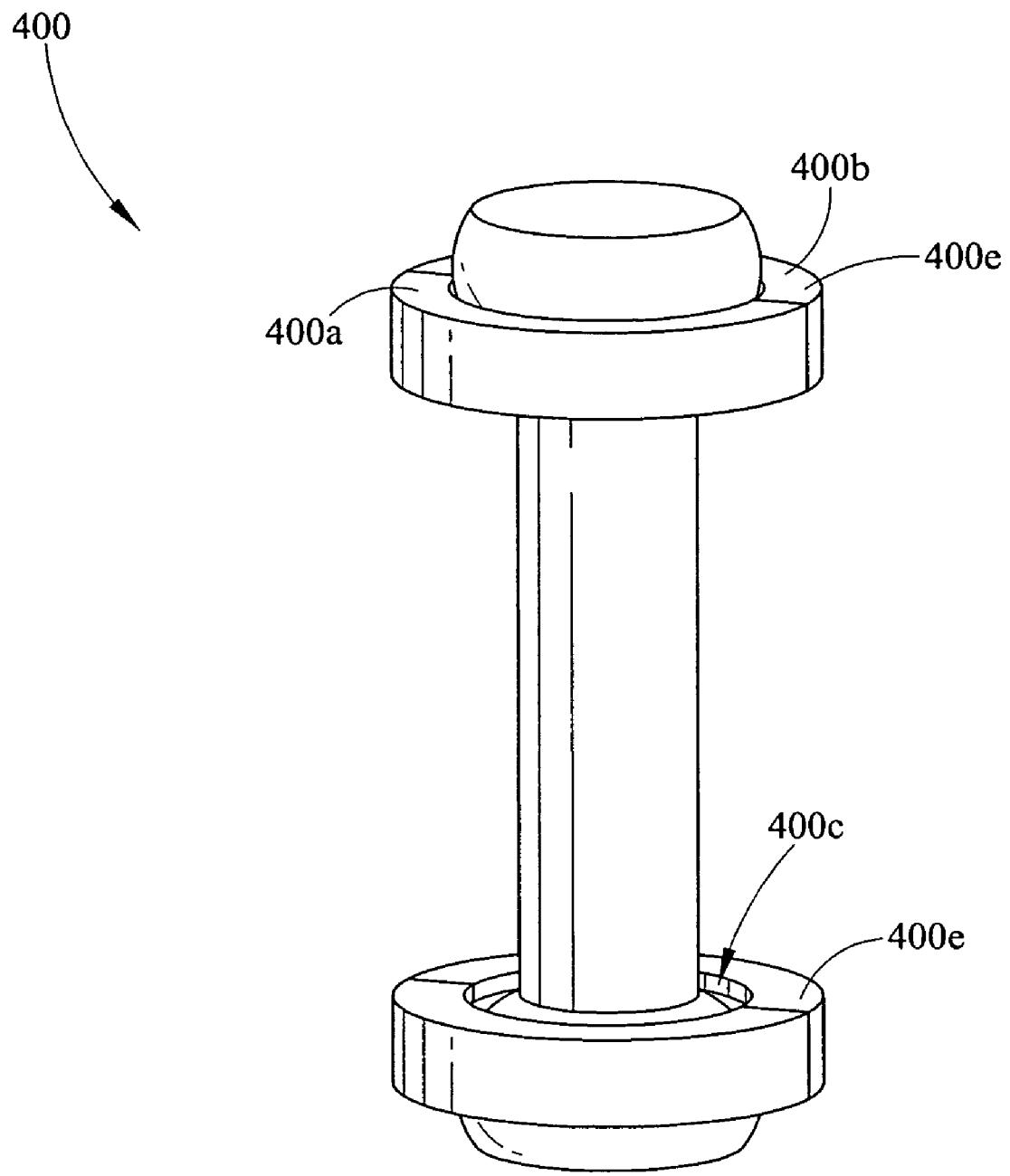
FIG. 24 is a perspective view of a motion-limiting member according to an embodiment of the invention incorporating a split ring in place around the enlarged portion of the motion-limiting member.

In bending, the motion-limiting members 80 can perform the primary or secondary motion limiting functions. Referring to FIG. 2, the most common bending scenario for the spine is bending in the sagittal plane (that is, bending about the x-axis). For example, this would be accomplished by bending over to tie one's shoes. As a bending moment is applied to the disc 10, the disc 10 can undergo both shear and lateral displacement. Referring now to FIGS. 21 and 23, a disc 10 is depicted in such a scenario and is shown exaggerated for easier reference. It can be seen that the anterior side is slightly compressed, while the posterior side is slightly in tension and a slight translation of the upper endplate 20 with respect the lower endplate 30. It can be seen that the motion-limiting members 80 can become oriented diagonally. In this event, the motion-limiting members 80 in tension provide a force preventing the upper endplate 20 and lower endplate 30 from separating because the lower surface 93 of the ball 91 begins to bear upon the split ring assembly 400 and/or bearing surfaces 272 of the openings 271. It should be noted that the mechanics of the disc 10 depicted in FIGS. 21 and 23, with reference to FIG. 2, are basically identical whether the bending is in the sagittal plane (front to back, or tying ones shoes) or in the frontal plane (side to side bending).

In flexion, which is the most important movement of an L4-L5 or L5-S1 disc, the motion-limiting members 80 are strategically oriented to resist the tension in the posterior region of the disc 10. When braided cables are used as the motion-limiting members 80, compression of the cables can cause splaying, which shortens their fatigue life. Therefore, placing more motion-limiting members 80 posteriorly than anteriorly (for example, see FIG. 12) accounts for the greater expected flexion moments of 20-30 N·m versus the lesser extension moments of about 10 N·m.

A further factor in the allowed range of motion in flexion and extension is a consideration of the cable distance from an assumed center of rotation at the center of the disc 10. The farther from the center, the greater the resisting moment, but the more initial slack necessary to allow the required 8-12 degrees of flexion. The more initial slack allowed, the more bending movement is allowed. Combinations of cable placement and initial diagonal orientation may be necessary to solve these conflicting design goals. Although greater ranges are certainly possible for the invention, preferable ranges of stiffnesses and motion for the disc 10 are as follows: Nonlinear stiffness in compression (1,000 to 3,000 N/mm) and in flexion (1.0 to 5.0 N·m/deg) and maximum motion in compression (1.0 to 2.0 mm) and in flexion (8 to 12 deg).

In one embodiment of the artificial intervertebral disc prosthesis (see FIGS. 14, 15, 16, 17, 18, and 19), four motion-limiting members are present. In this embodiment, there are corresponding four openings 271, 371 in both the upper and lower subplates, 200, 300. One of the openings 271, 371 is located anteriorly and slightly to the left of the first and second projections 270, 370, while another opening 271, 371 is located anteriorly and slightly to the right of the first and second projections 270, 370. Similarly, a third opening 271, 371 is located posteriorly and slightly to the left of the first and second projections 270, 370, while the fourth opening 271, 371 is located posteriorly and slightly to the right of the first and second projection 270, 370. In this embodiment, when the disc 10 is in flexion, the most important movement of an L4-L5 disc, the motion-limiting members 80 at the posterior portion of the disc 10 are strategically-oriented to resist the tension in the posterior region of the disc 10, while the motion-limiting members 80 at the anterior portion of the disc 10 float freely in the spike cavity in the anterior region of the disc 10. However, a disadvantage of this embodiment is the presence of motion-limiting members 80 at the anterior portion of the disc 10. As discussed above, when braided cables are used for the motion-limiting members 80, compression can cause splaying, leading to a shorter fatigue life. As motion-limiting members 80 located at the anterior of the disc 10 encounter significantly more compression than motion-limiting members 80 located at the posterior of the disc 10 during the normal activity patterns of most individuals, anteriorly-located motion-limiting members 80 are likely to have a shorter life than those located at the posterior of the disc 10.

Another embodiment of the artificial disc intervertebral prosthesis is envisioned in which no motion-limiting member 80 is present. Instead, the compression stop formed by the first and second projections 270, 370 also limits motion in flexion and lateral bending. This is accomplished by sizing the first and second projections 270, 370 such that when the prosthesis engages in flexion or bending and the first projection 270 tilts toward the second projection 370, the leading edge of the first projection 270 will come into contact with the second projection 370 after a predetermined amount of flexion or bending, preventing further motion. This has the advantage of eliminating the need for the motion-limiting members 80, thereby reducing the number of elements within the prosthesis that are susceptible to wear and fatigue.

The preferred disc 10 has certain load versus deflection characteristics that are similar to those found in the natural human disc. As was stated above, it is useful, once implanted, that the surgeon and patient can know the state of load experienced by the device. In this regard, referring to FIG. 25, embodiments of the disc have, integral to its construction, strain gauges 41 or other means of force or pressure transduction. For illustration purposes only, not to be construed as limiting the invention thereto, the discussion will be directed to the use of strain gauges 41. An electronics package 380 having a transducer can be connected to signal conditioning and amplification circuitry on a micro scale in order to fit within the constraints of space available in the upper or lower endplate 20, 30. In this embodiment, the center stop is integral to the lower endplate 30 and consists of a hollow raised cylindrical platform 381. The space inside this raised platform 381 can house, for example, a 3×3×3 mm electronics package 380. The package can be wired to strain gauges 41 on the inside of the raised cylinder and in peripheral locations around the bottom endplate 30. Alternatively, the transduction means can be connected to electronics 380 such as piezo-electronics that eliminate the need for signal conditioning and amplification.

Figure 25:
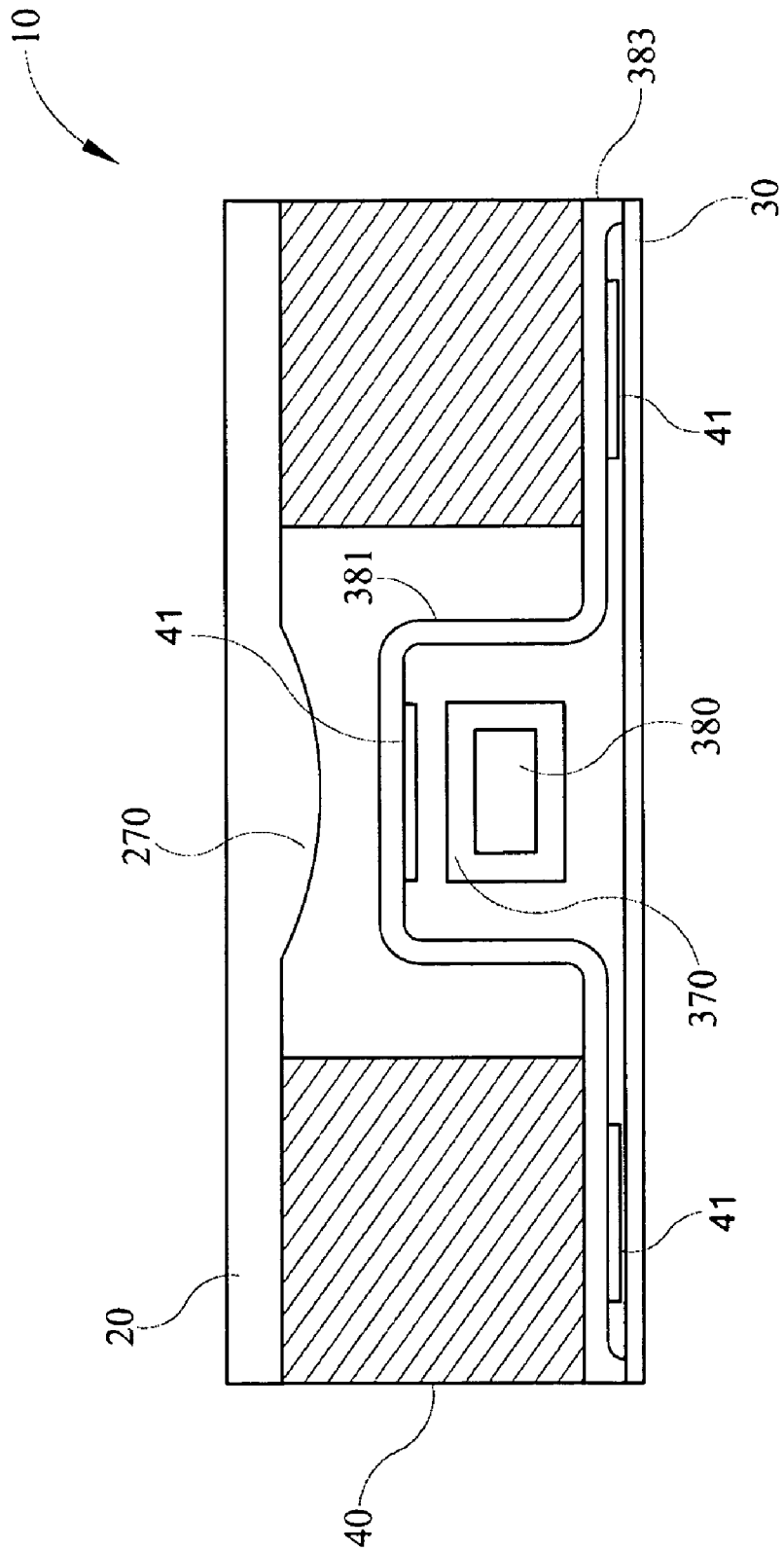
FIG. 25 is a side elevation schematic of an embodiment of an artificial disc using strain gauges to provide force transduction for providing data to locations external to the disc.

Referring now to FIG. 25, there is shown an endplate having an internal region defined on one side by part of the endplate 30 and on an opposite side by a layer 383 that may connect with a compression stop. There may be a force transducer 41, such as a strain gauge, in the interior region directly adjacent to where the polymer (elastomer) 40 adjoins the endplate 30. There may be a force transducer 41, such as a strain gauge, inside the compression stop. Inside the compression stop there may also be other electronics 380 such as a microelectromechanical system, signal conditioning, telemetry, or a coil. The layer 383 together with the rest of the endplate 30 may form a hermetic seal enclosing electronics 380 within the internal region. The layer 383 may be laser-welded to the rest of the endplate 30. Other types of force transducers 41 include piezoelectric sensors.

Figure 22:
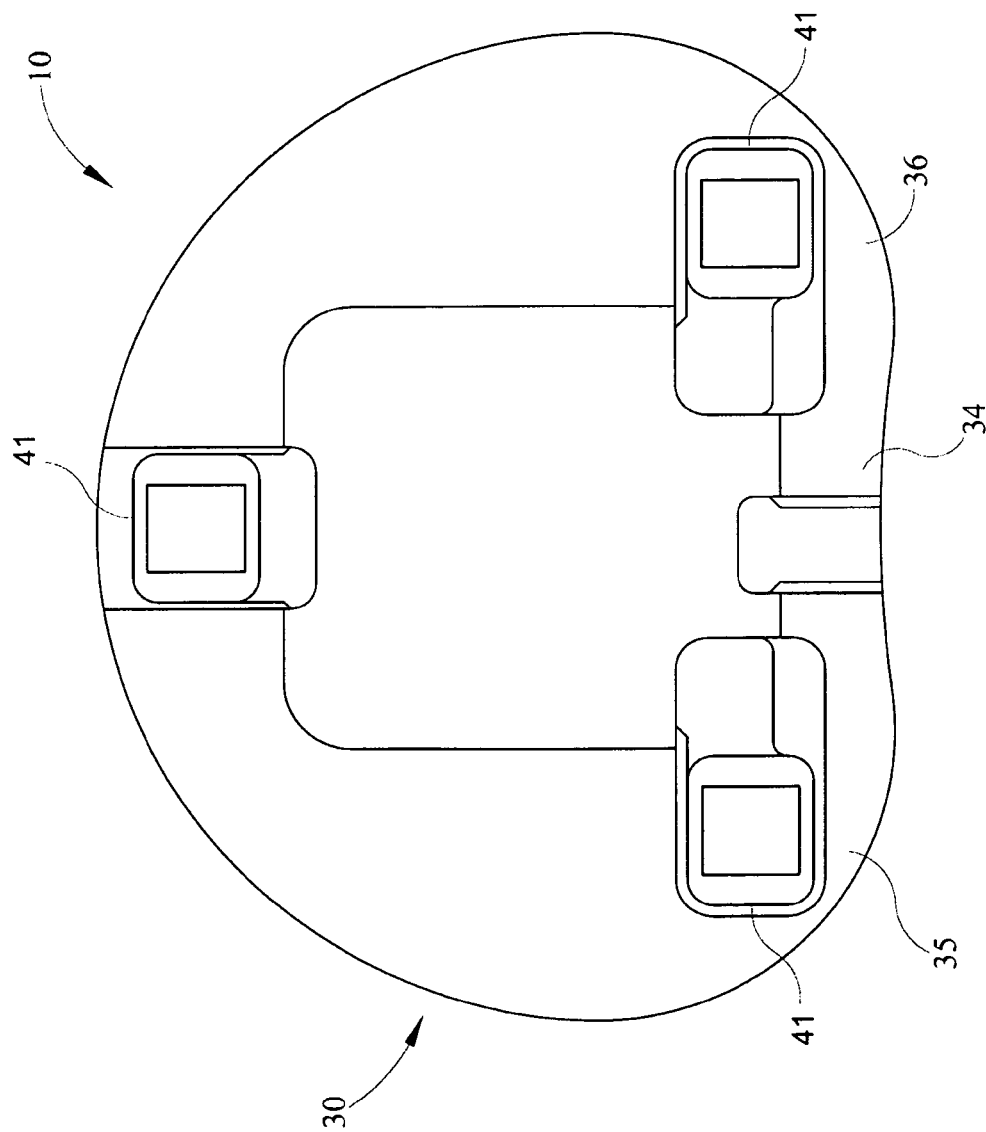
FIG. 22 is a top view of an embodiment of a lower endplate flex circuit for an artificial disc using strain gauges to provide force transduction for providing data external to the disc.

Since the center stop cylinder is not in contact with the polymer, the strain gauge 41 placed there will only measure contacts between the upper endplate and the center stop on the lower endplate. This data is useful in itself as an indicator of when loads are sufficiently high to engage the stop mechanism. However, in addition, more continuous data is available from peripherally placed strain gauges 41 that will measure stress in the endplate caused by compression, bending, torsion, and shear loads in all directions. This information can give a precise measure of the magnitude and direction of loads on the disc. FIGS. 22 and 25 depict how one embodiment of an artificial disc 10 uses strain gauges 41 to measure the load experienced by the prosthesis and relay that data on demand.

Placing the transducers within the polymer is not preferred since fatigue of wires or the introduction of stress risers within the polymer can lead to fatigue failure initiation sites. For these reasons, placing the signal conditioning microelectronics 380 within the center compression stop is advantageous. Once conditioned, the signal is telemeterized on demand through excitation of an internal coil from an inductively coupled external coil (not shown). This couple energizes the electronics 380 and transmits the data upon request. This mode of interrogating the device for its load condition can be done real time. In addition, the electronics package 380 may be provided with a data storage element capable of storing load history according to a preset sampling routine. Thus in interrogating the device, data may be fed back from memory storage. It is also possible to sample the device remotely and wirelessly via the internet.

The data can indicate changes in the device since its implantation. It can also store load history to indicate if the patient is following doctor's orders for allowed activities. The power source for the memory-based data storage element is optionally a micro battery or a capacitor charged from the external inductive couple. The micro battery or capacitor may be part of the electronics package and may optionally be stored in the raised platform 381. The use of piezos is also possible. In one embodiment, a mylar flex circuit is pre-made and placed on the second endplate. Transducers or load or pressure sensors 41 may be embedded on the mylar flex circuit and connected to the signal conditioning and amplifying electronics.

Figure 26:
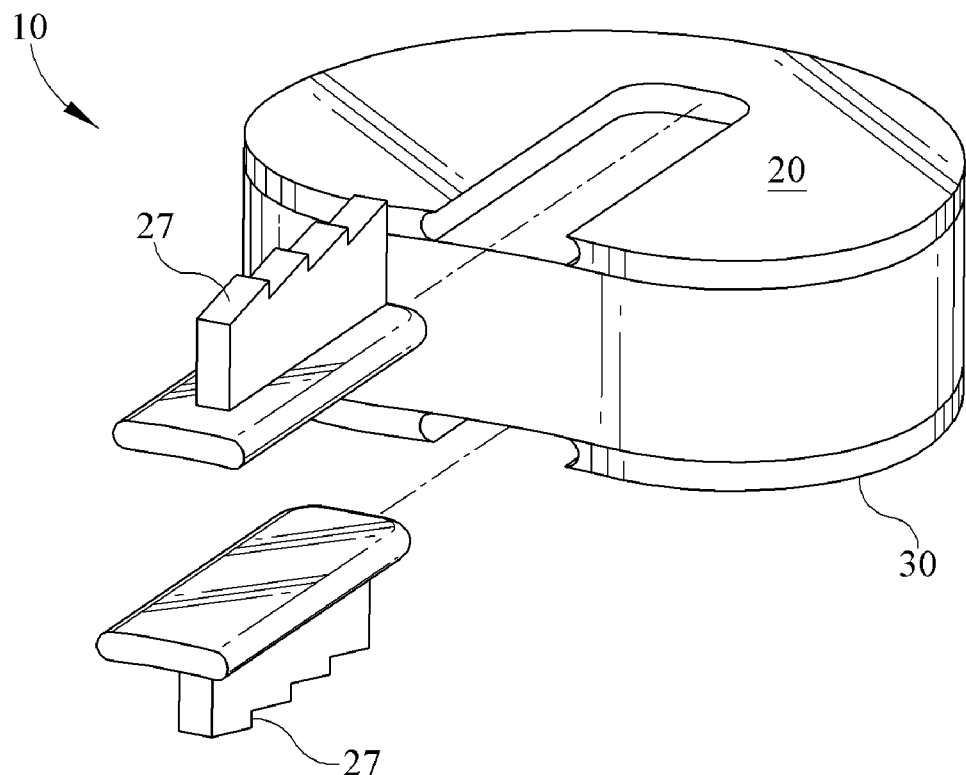
FIG. 26 is a perspective view of the posterior side of an alternative embodiment of the disc showing removable appurtenances.
Figure 27:
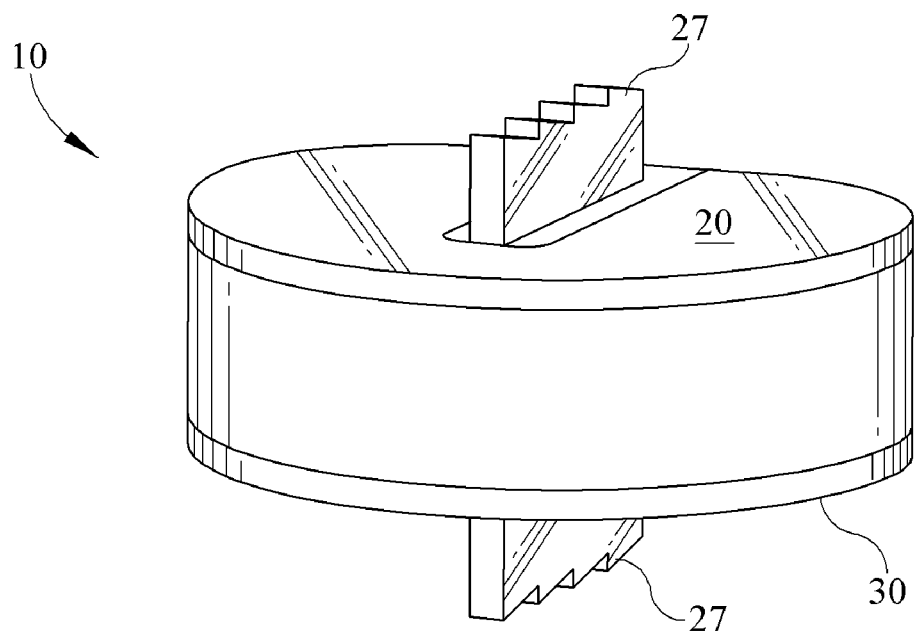
FIG. 27 is a perspective view of the anterior side of the disc shown in FIG. 26.
Figure 28:
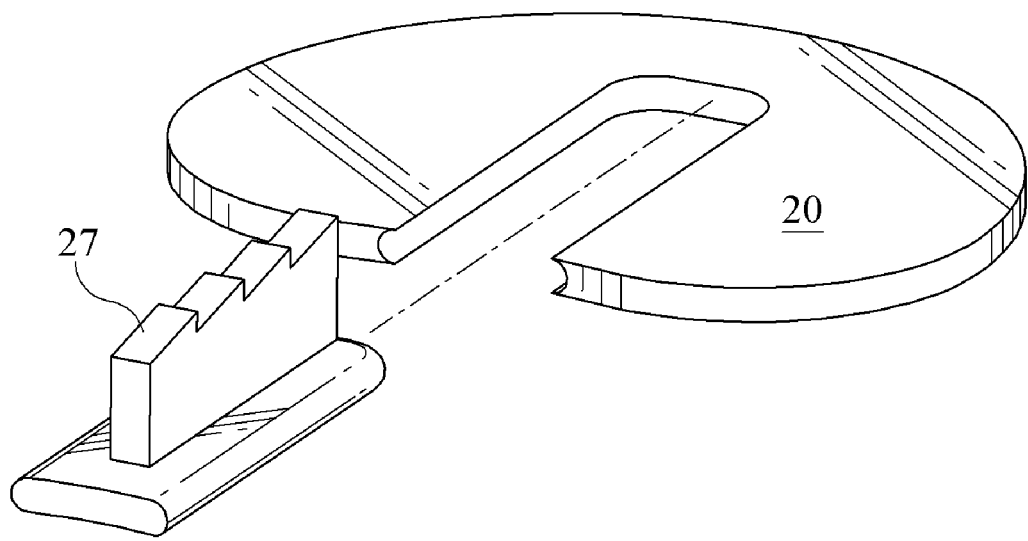
FIG. 28 is a perspective view of the posterior side of an appurtenance and an upper endplate according to an embodiment of the invention.
Figure 29:
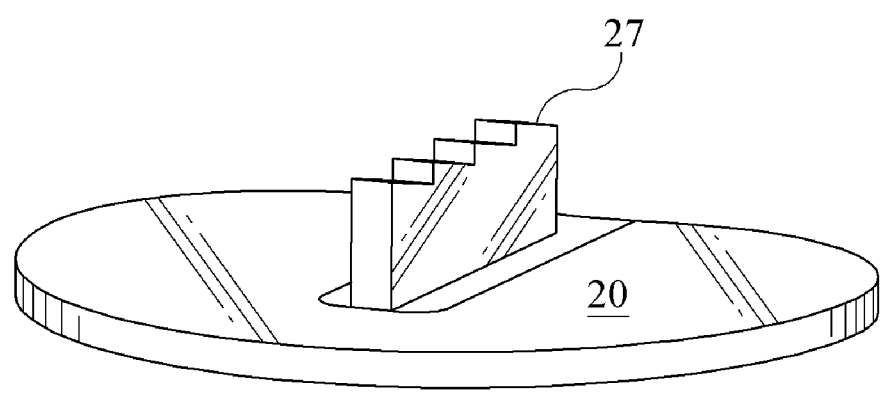
FIG. 29 is a perspective view of the anterior side of the endplate shown in FIG. 28.

FIGS. 26-29 show an alternative embodiment of the invention wherein the disc 10 comprises multiple components that may be implanted separately. Indeed, the disc 10 may comprise many forms and embodiments that are implantable in pieces. The desirability of multi-part prostheses is known by surgeons and simplifies the implantation procedures. FIGS. 26-29 simply depict one example. In these figures, the appurtenances 27 are removably insertable into the upper and lower endplates 20, 30. In FIG. 26 the upper surface 92 of the balls 91 is not depicted but typically would be visible. Preferably, the groove into which appurtenances 27 are slid form a taper lock fit to lock the appurtenance into place. One example of a surgical procedure using a multi-part disc 10 involves the surgeon first removing the diseased or damaged disc using the typical procedures in practice. An instrument (not shown) is used to prepare the site by cutting grooves into the adjacent vertebrae to receive the appurtenances 27 of the disc 10. Preferably the instrument cuts both the upper and lower grooves simultaneously so as to maintain the tolerances needed for the implantation of the disc 10. An instrument then inserts the appurtenances 27 into the prepared site. The disc 10 is then inserted between the appurtenances 27, which receive the grooves of the upper and lower endplates 20, 30. The taper lock secures the appurtenances 27 to the prosthesis.

Many possibilities exist for the manufacturing and the materials involved in an artificial intervertebral disc prosthesis according to the present invention. The endplates 20, 30 and/or endplate subplates 200, 300 may be of the materials described above. Further, they may have thicknesses in the range of approximately 1 mm to approximately 3 mm. Their surfaces may be surface-treated or machined for texture and bonding improvement. Examples of such treatments include but are not limited to ion etching, simple grit blasting, plasma spraying, or CNC machined geometry. Preferably the endplates 20, 30 (and/or 200, 300) are a CCM which is good in wear. The upper surfaces 21, 210 of the upper endplate 20 and upper subplate 200, and the lower surfaces 31, 310 of the lower endplate 30 and lower subplate 300, as well as the surfaces that interact with the visco-elastic cushion, may be coated with Titanium 6Al4V to improve bone interface and bonding. The second projection 370 can, as stated above, take many forms, including by way of mere examples, a cylinder, a post, a platform, and so forth. The preferred cylindrical member 381 is a solid projection from the lower endplate 20 or lower subplate 200. However, the cylindrical member 381 could be hollow so as to accommodate integral microelectronics diagnostics 380, as was discussed above.

Manufacturing the disc 10 can be accomplished in a variety of manners. Preferably, the endplates 20, 30 are first machined of either titanium or cobalt chrome molybdenum (CCM), with openings 270 representing areas where there will be no elastomer cushion 40. The endplates 20, 30 are inserted into a mold with cores to create voids that will later contain the center stop and the motion-limiting members 80. It is preferable to keep the elastomer free of the cables and center stop so as not to introduce elastomer abrasion leading to fatigue failures. The motion-limiting members 80 are then assembled to the molded subassembly with a welding process. The cable assemblies terminate in a ball end. In the preferred embodiment the ball is preformed onto the cable, though this is not required.

Figure 3A:
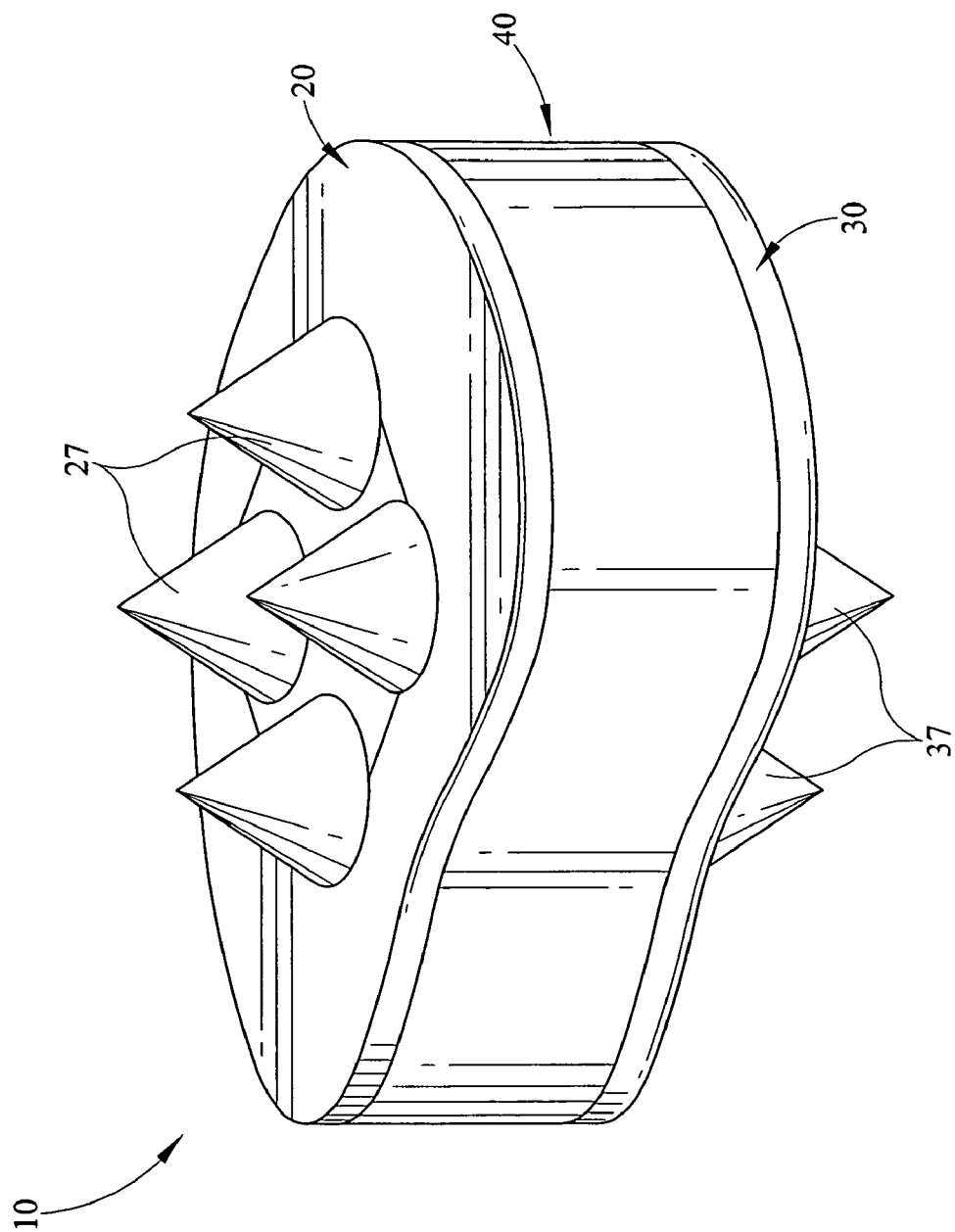
Figure 3B:
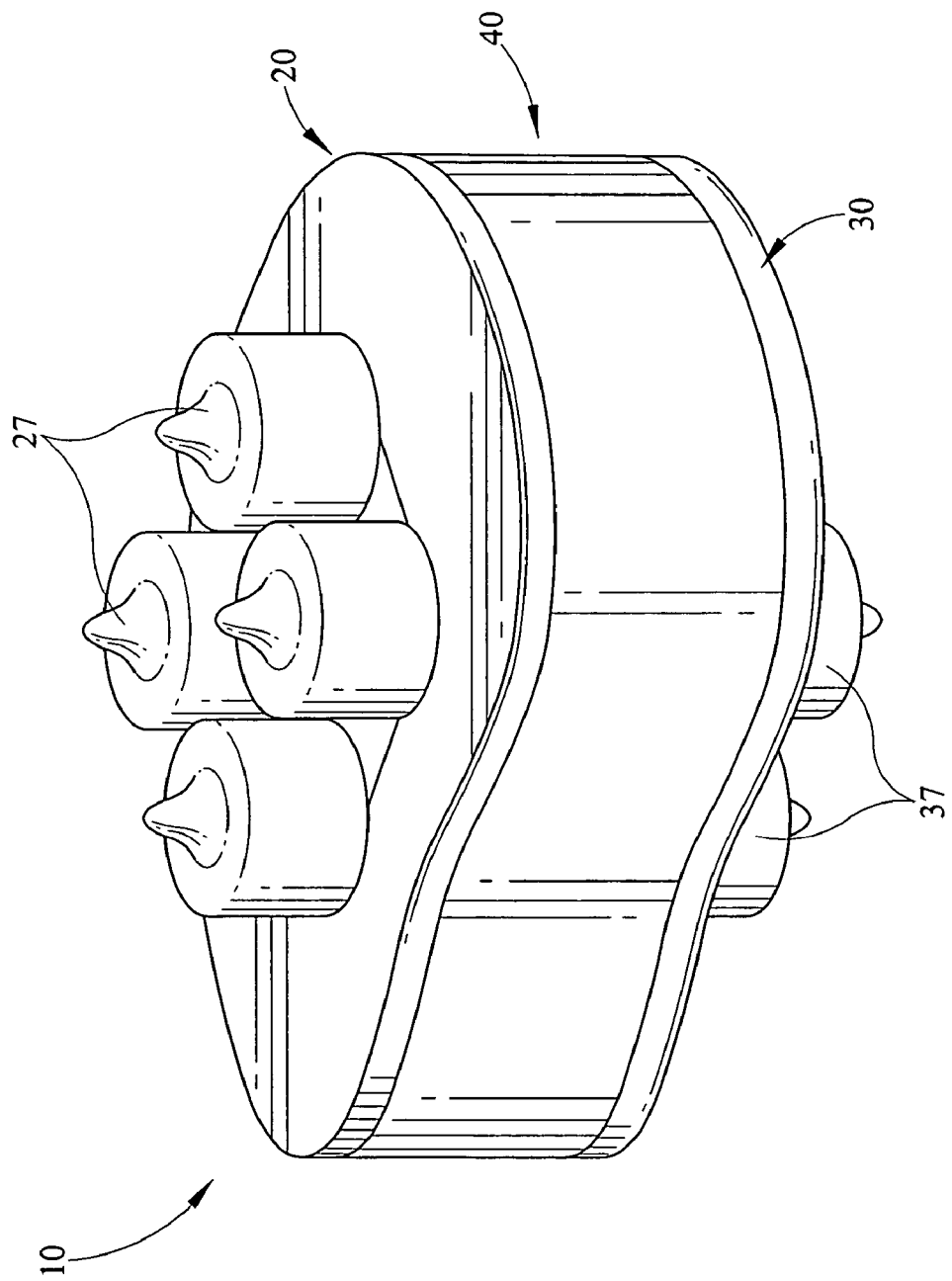
Figure 3C:
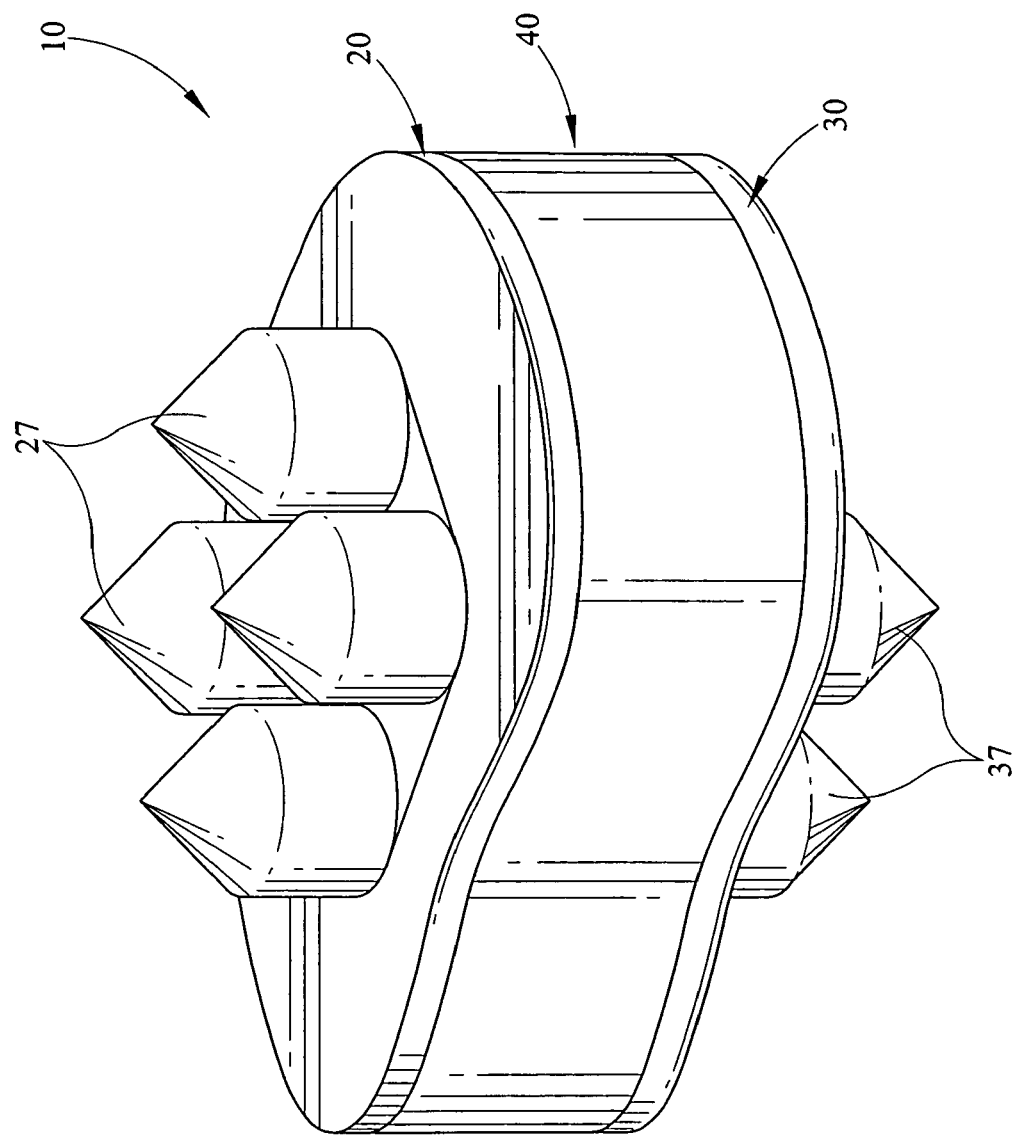
Figure 4:
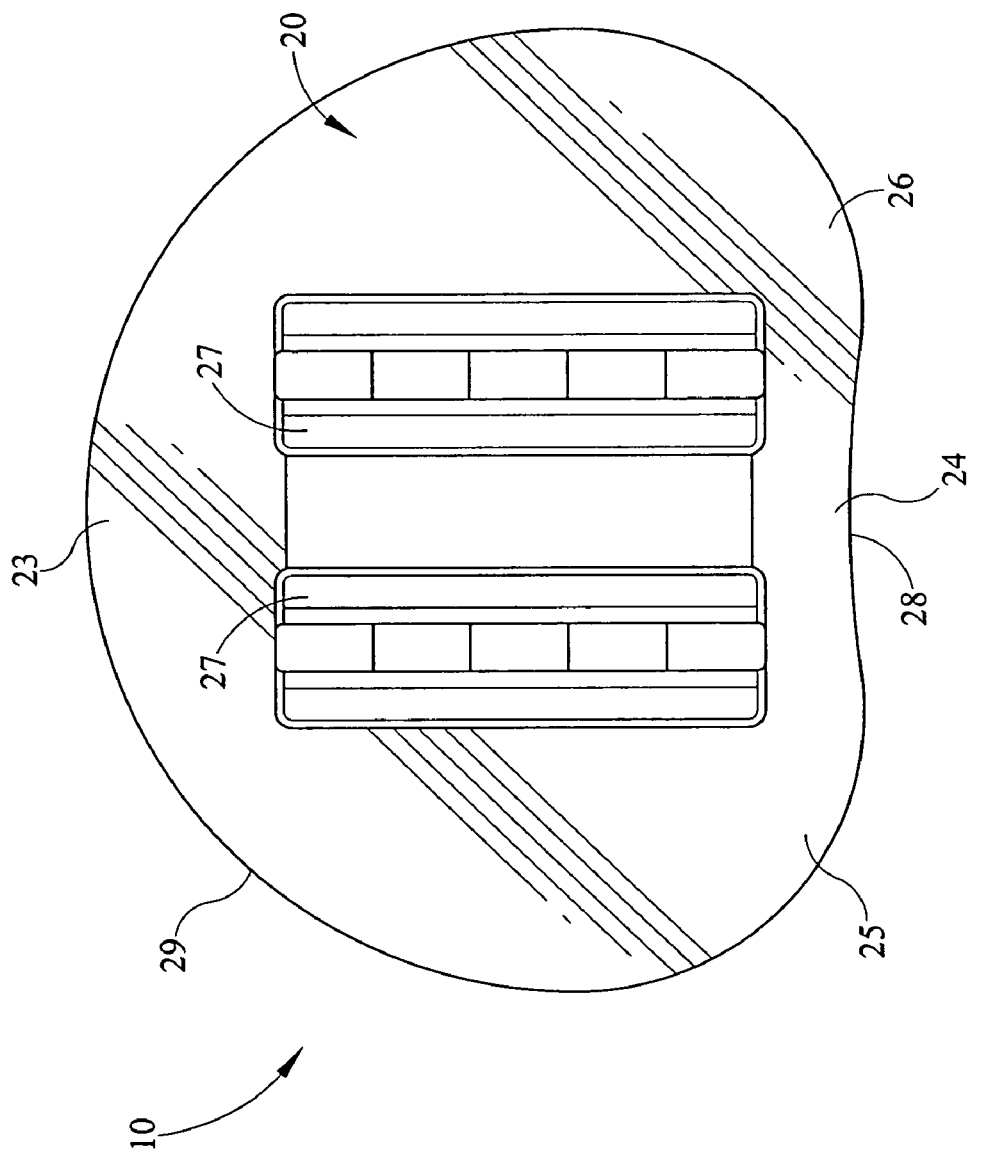
FIG. 4 is a top plan view of the artificial disc of FIG. 3.
Figure 5:
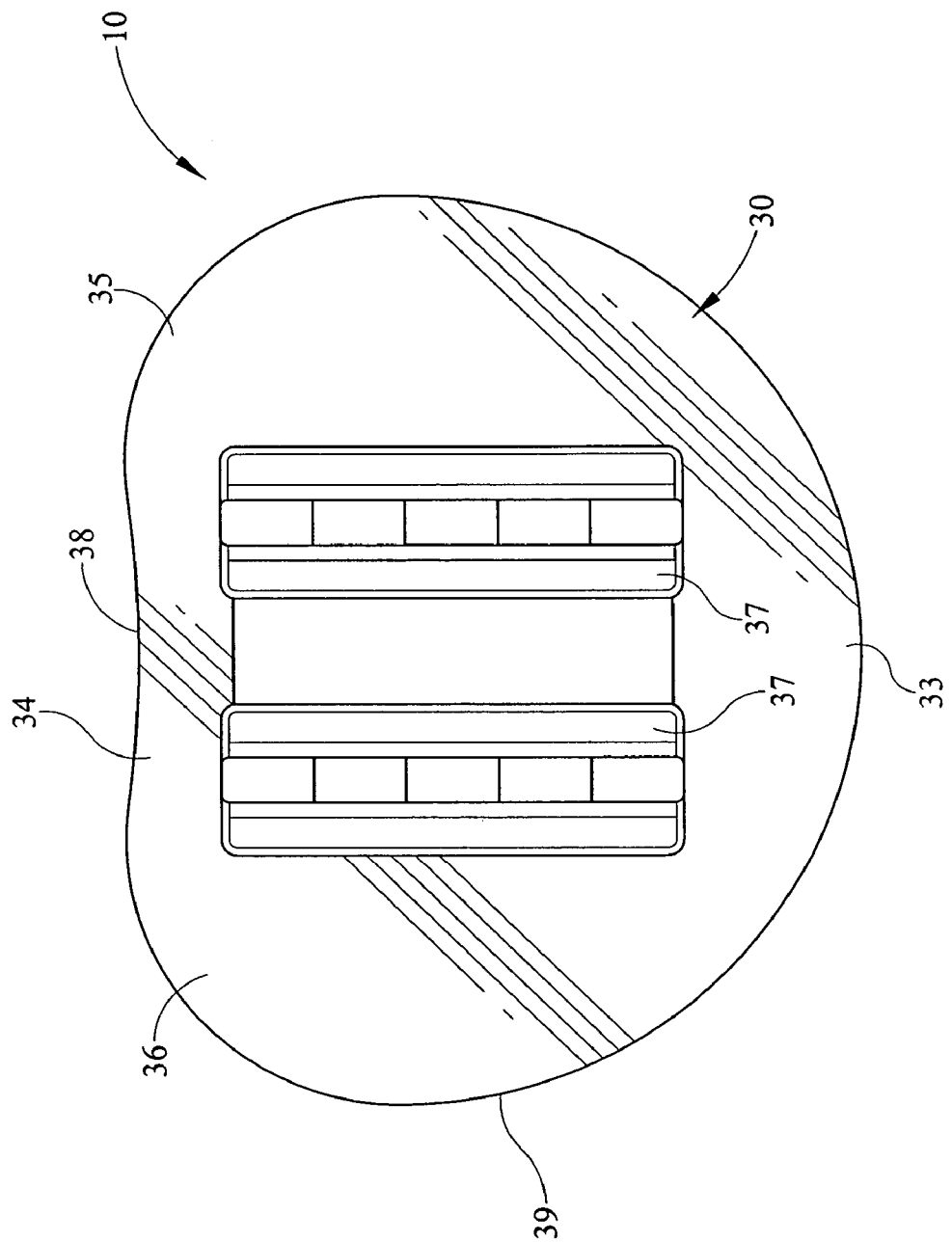
FIG. 5 is a bottom plan view of the artificial disc of FIG. 3.
Figure 6:
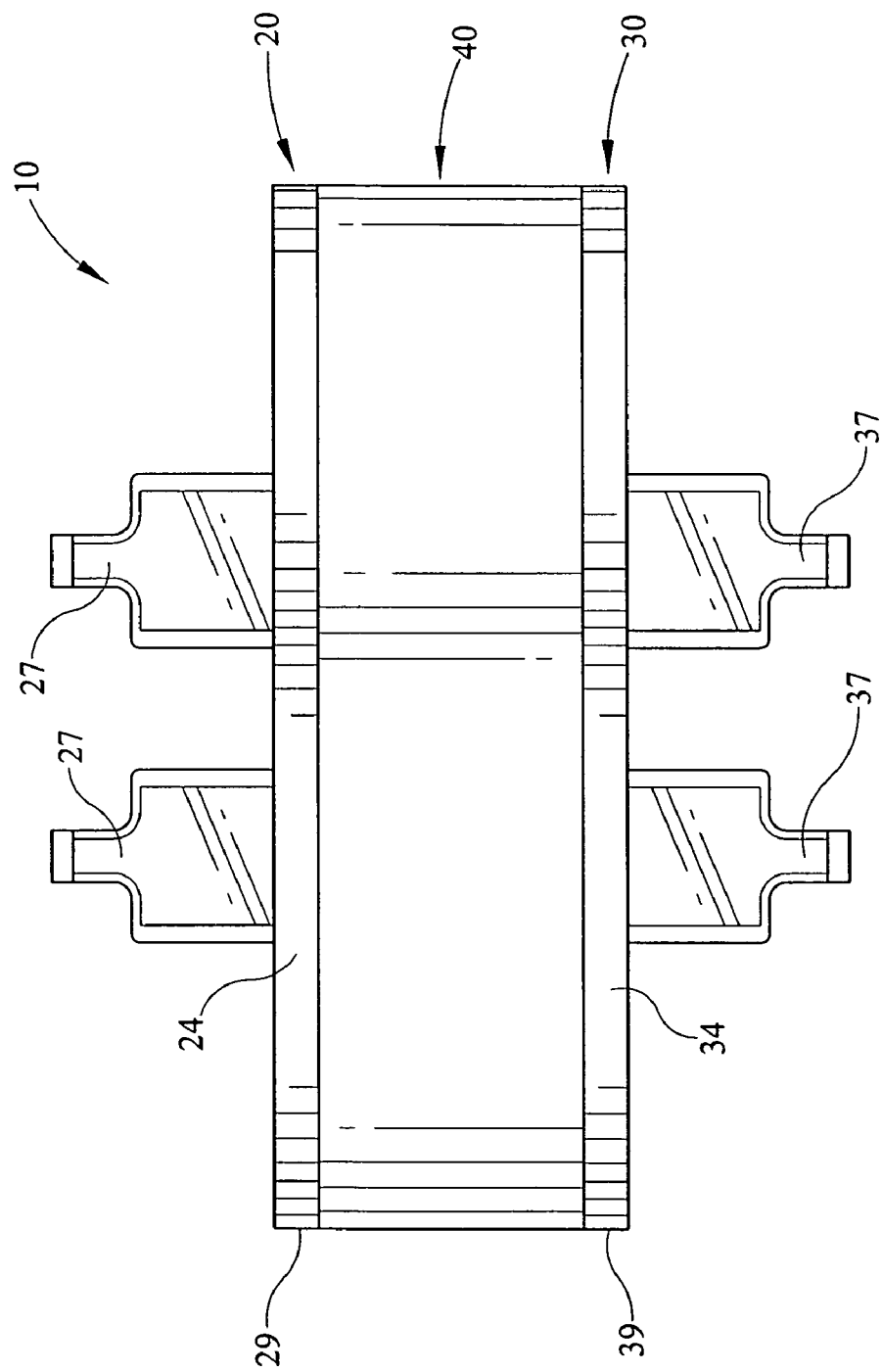
FIG. 6 is a posterior elevation view of the artificial disc of FIG. 3.
Figure 7:
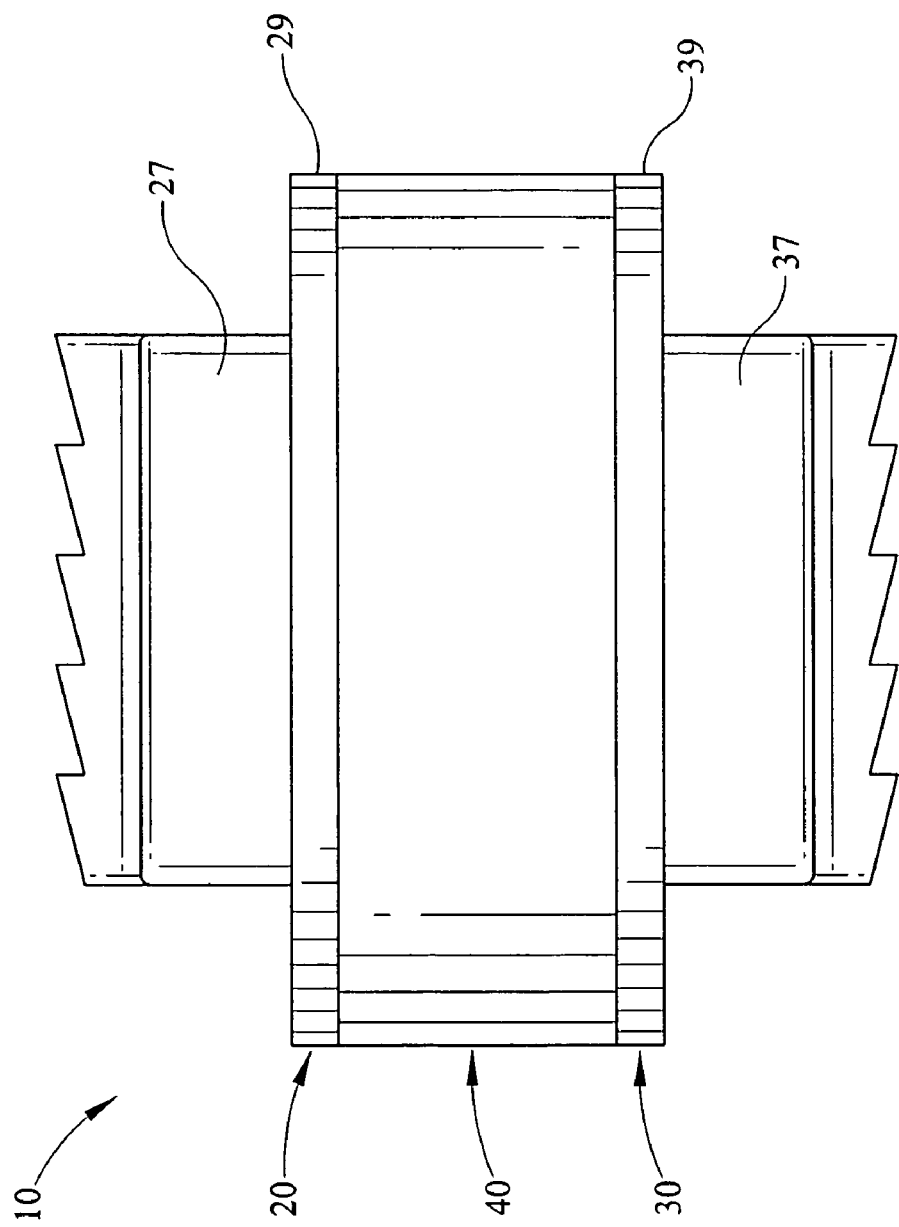
FIG. 7 is a lateral elevation view of the artificial disc of FIG. 3.

These ball-cable assemblies are then inserted into the endplates 20, 30 with the split ring assemblies 400 as described above. In those embodiments not utilizing split ring assemblies 400, the ball-cable assemblies are inserted into the endplates 20, 30 as described above. Preferably, over each ball location on the upper endplate 20 and on the lower endplate 30 are appurtenances 27, 37, respectively. These appurtenances are shown in FIG. 3 as keels, but they could be individual conical spikes as shown in FIG. 3(a) or other appurtenances, for example FIGS. 3(b) and 3(c). For those embodiments where the enlarged portion 90 extends beyond the plane of the upper surface 21 of the upper endplate 20 or the lower surface 32 of the lower endplate 30, these appurtenances serve as temporary anchors in the vertebra and covers that enclose the mini ball-socket joint created between the endplate and the ball. Additionally, the ball-socket articulation prevents bending in the cables, thereby extending fatigue life. In certain embodiments utilizing many motion-limiting members 80, it is possible for the motion-limiting members 80 to be laser welded into the endplates in the openings where cores created voids in the elastomer.

As stated above, the center stop is a designed gap preferably to prevent more than 1-2 mm of compression from occurring, thereby limiting the elastomer compressive stress. This mandates a good wear interface for the stop. A choice of CCM on CCM is preferred due to its recent introduction as the wear couple in some FDA-approved metal-on-metal hips. Also as stated, many structural configurations for the first and second protrusions 270, 370 are possible, including pin-on-pin, pin-on-plate (shown), plate-on-plate, ball-on-plate, and so forth. The elastomer will exclusively carry the load during most activities of daily living. The center stop will be engaged only during activities of high exertion, except in the embodiment in which no motion-limiting members 80 are present.

While there has been described and illustrated particular embodiments of a novel artificial disc prosthesis, and in particular, a visco-elastic constrained motion disc, it will be apparent to those skilled in the art that variations and modifications may be possible without deviating from the broad spirit and principle of the present invention, which shall be limited solely by the scope of the claims appended hereto.

The invention claimed is:

1. A spinal disc prosthesis, comprising:
 a first endplate and a second endplate, each of said first endplate and said second endplate having a respective bone-contacting surface for attaching to respective vertebrae and a respective non-bone-contacting surface opposite said respective bone-contacting surface;
 a polymeric member interposed between and adhered to said non-bone-contacting surfaces of said respective endplates;
 a compression stop having a first substantially planar uninterrupted contact surface on a surface facing said second endplate, and a second substantially uninterrupted contact surface on a surface facing said first endplate;
 wherein in a first position, said first substantially planar uninterrupted contact surface does not contact said second substantially uninterrupted contact surface, and said first endplate and said second endplate are substantially unconstrained to relative movement about six degrees of freedom; and
 wherein in a second position, said first substantially planar uninterrupted contact surface contacts said second substantially uninterrupted contact surface, and said first endplate and said second endplate are substantially constrained against relative translation in one direction along the cephalad-caudal axis, but are substantially unconstrained in relative translation and rotation about all other axes; and
 electronics contained within said compression stop.

2. The spinal disc prosthesis of claim 1, wherein said electronics are hermetically sealed within said compression stop.

3. A spinal disc prosthesis, comprising:
 a first endplate and a second endplate, each of said first endplate and said second endplate having a respective bone-contacting surface for attaching to respective vertebrae and a respective non-bone-contacting surface opposite said respective bone-contacting surface;
 a polymeric member interposed between and adhered to said first and second endplates, wherein said polymeric member has an annular shape having an empty central region defining an interior of said polymeric member;
 at least one member on a non-bone-contacting surface of one of said first or second endplates, said member having at least one surface parallel to a longitudinal axis of said prosthesis and suitable to transmit force between said first and second endplates under at least some conditions, said member being located at least partially within said empty central region of said polymeric member; and
 at least one flat force sensor positioned within one of said first endplate or said second endplate, wherein said sensor has a direction of force measurement that is oriented in a predetermined direction relative to said prosthesis;
 wherein said prosthesis comprises three of said sensors located at locations that form vertices of a triangle; and
 wherein one of said sensors is located substantially on an anterior-posterior centerline of said prosthesis and two other of said sensors are located one on each side of said anterior-posterior centerline.

4. The prosthesis of claim 3, wherein said prosthesis permits relative motion between said first endplate and said second endplate.

5. The prosthesis of claim 3, wherein said sensor is located within said first endplate.

6. The prosthesis of claim 3, wherein said prosthesis comprises two of said sensors.

7. The prosthesis of claim 3, wherein said prosthesis comprises two of said sensors that are located one on each side of an anterior-posterior centerline of said prosthesis.

8. The prosthesis of claim 3, wherein said prosthesis comprises two of said sensors that are Located at locations which are symmetric with respect to an anterior-posterior centerline of said prosthesis.

9. The prosthesis of claim 3, wherein said prosthesis comprises three of said sensors.

10. The prosthesis of claim 3, wherein said triangle is substantially an isosceles triangle.

11. The prosthesis of claim 3, wherein one of said sensors is located substantially on an anterior-posterior centerline of said prosthesis and two other of said sensors are located one on each side of said anterior-posterior centerline at locations which are symmetric with respect to said anterior-posterior centerline.

12. The prosthesis of claim 3, wherein said sensor is selected from the group consisting of a strain gauge and a piezoelectric sensor.

13. The prosthesis of claim 3, wherein said sensor measures a force exerted by a member that bears at least a portion of any load that is applied to said prosthesis.

14. The prosthesis of claim 3, wherein said sensor measures a force exerted on a member that bears load only when a first component of said prosthesis is touched by a second component of said prosthesis.

15. A spinal disc prosthesis, comprising:
 a first endplate and a second endplate, each of said first endplate and said second endplate having a respective bone-contacting surface for attaching to respective vertebrae and a respective non-bone-contacting surface opposite said respective bone-contacting surface;
 a polymeric member interposed between and adhered to said first and second endplates;
 a first non-deforming component connected to said first endplate; and a first flat sensor configured to only measure a force that is experienced by said first non-deforming component after a predetermined relative displacement of said first endplate and said second endplate has been reached.

16. The spinal disc prosthesis of claim 15, further comprising a second flat sensor, wherein said second flat sensor is configured to measure a force exerted by a member that bears at least a portion of any load that is applied to said prosthesis.

17. A spinal disc prosthesis, comprising:
a first endplate and a second endplate each attachable to respective vertebrae;
at least one member suitable to transmit force between said first and second endplates under at least some conditions; and
at least three force sensors associated with one of said endplates and located at locations that form vertices of a triangle,
wherein a first one of said sensors is located substantially on a plane of symmetry of said prosthesis and two other of said sensors are located one on each side of said plane of symmetry, and wherein said three sensors are non-collinear with each other.

18. A spinal disc prosthesis, comprising:
a first endplate and a second endplate each suitable to attach to respective vertebrae; and
a polymeric member interposed between and adhered to said first and second endplates, wherein said polymeric member has an annular shape having an empty central region defining an interior of said polymeric member,
wherein said first endplate comprises a hermetically sealed cavity,
wherein said hermetically sealed cavity comprises a short region having a short region boundary, and a tall region having a tall region boundary,
wherein a portion of said short region boundary of said hermetically sealed cavity is adhered to said polymeric member,
wherein at least a portion of said tall region of said hermetically sealed cavity partially occupies said empty central region of said polymeric member,
further comprising a sensor located in said short portion of said hermetically sealed cavity and
further comprising electronics located in said tall portion of said hermetically sealed cavity.

19. A spinal disc prosthesis, comprising:
a first endplate and a second endplate each suitable to attach to respective vertebrae; and
a polymeric member interposed between and adhered to said first and second endplates, wherein said polymeric member has an annular shape having an empty central region defining an interior of said polymeric member,
wherein said first endplate comprises a hermetically sealed cavity,
wherein said hermetically sealed cavity comprises a short region having a short region boundary and a tall region having a tall region boundary,
wherein a portion of said short region boundary of said hermetically sealed cavity is adhered to said polymeric member,
wherein at least a portion of said tall region of said hermetically sealed cavity partially occupies said empty central region of said polymeric member,
wherein at unloaded conditions said tall region of said hermetically sealed cavity does not contact said second endplate, but if said first endplate and said second endplate are sufficiently close to each other, said tall region of said hermetically sealed cavity contacts said second endplate and receives load from said second endplate.

20. A spinal disc prosthesis, comprising:
a first endplate and a second endplate each suitable to attach to respective vertebrae,
wherein said first endplate comprises a component capable of receiving force exerted by said second endplate or a member connected to said second endplate, said first component further comprising an enclosure;
wherein said first endplate comprises a first layer and a second layer separate from said first layer and facing said first layer;
wherein said first endplate further comprises at least one force sensor, wherein said at least one force sensor is hermetically enclosed within said enclosure; and
wherein, when assembled, said first layer, said at least one force sensor, and said second layer are encompassed within a first thickness that is no larger than a thickness of said first endplate; and
wherein said first thickness is dimensioned parallel to a longitudinal axis of said prosthesis when viewing said prosthesis from an angle normal to said longitudinal axis.

21. The spinal disc prosthesis of claim 20, wherein said enclosure comprises a first flat surface and a second flat surface opposed to said first flat surface, at least a portion of said first flat surface being adhered to said polymeric member, and said second flat surface being a continuous substantially flat uninterrupted surface substantially parallel to said portion of said first flat surface that is adhered to said polymeric member.

22. A spinal disc prosthesis, comprising:
a first endplate and a second endplate each suitable to attach to respective vertebrae;
wherein said first endplate comprises a first layer and a second layer, at least part of said second layer being substantially parallel to said first layer, and a flat region between said first layer and said second layer, said first layer and said second layer being joined to each other at an outer edge;
a polymeric member interposed between and adhered to said second endplate and to said first layer of said first endplate; and
a sensor, positioned suitably to measure a force exerted by said polymeric member on said first endplate in a vicinity of said sensor, wherein said sensor has a flat shape aligned substantially parallel to said first layer;
wherein said first layer has a first surface in contact with said polymeric member and a second surface opposite said first surface, said sensor being in contact with said second surface.

23. The prosthesis of claim 22, wherein said sensor is located inside said first endplate.

24. The prosthesis of claim 22, further comprising a metal layer between said sensor and said polymeric member.

25. A spinal disc prosthesis, comprising:
a first endplate and a second endplate each suitable to attach to respective vertebrae;
at least one member suitable to transmit force between said first and second endplates under at least some conditions; and
wherein at least one of said endplates has a kidney-bean shape having a concavity, a convexity opposed to said concavity, and a first lobe and a second lobe, said first lobe and said second lobe being opposed to each other, and wherein a first force transducer is located at least partially within said convexity and a second force transducer is located at least partially within said first lobe and a third force transducer is located at least partially within said second lobe;

wherein a first linear axis extends between said second and third force transducers, and a second linear axis bisects and is normal to said first axis;

said first force transducer is positioned on or at a first distance from said second axis, and said second and third force transducers are positioned at a second distance from and on either side of said second axis;

wherein said second distance is greater than said first distance.

26. The spinal disc prosthesis of claim 25, wherein said prosthesis has a plane of symmetry passing through said concavity and said convexity, and said first force transducer is located closer to said convexity than are said second force transducer and said third force transducer.

* * * * *